United States Patent
Chae et al.

(10) Patent No.: US 11,591,306 B2
(45) Date of Patent: Feb. 28, 2023

(54) VITAMIN E-BASED AMPHIPATHIC COMPOUND, AND USE THEREOF

(71) Applicant: Industry-University Cooperation Foundation Hanyang University Erica Campus, Ansan-si (KR)

(72) Inventors: Pil Seok Chae, Ansan-si (KR); Ehsan Muhammad, Bhimber (PK)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 421 days.

(21) Appl. No.: 16/756,494

(22) PCT Filed: Feb. 28, 2018

(86) PCT No.: PCT/KR2018/002462
§ 371 (c)(1),
(2) Date: Apr. 16, 2020

(87) PCT Pub. No.: WO2019/088374
PCT Pub. Date: May 9, 2019

(65) Prior Publication Data
US 2020/0299252 A1 Sep. 24, 2020

(30) Foreign Application Priority Data
Nov. 1, 2017 (KR) ........................ 10-2017-0144694

(51) Int. Cl.
*C07D 311/72* (2006.01)
*C07H 15/26* (2006.01)

(52) U.S. Cl.
CPC ........... *C07D 311/72* (2013.01); *C07H 15/26* (2013.01)

(58) Field of Classification Search
CPC ............................. C07D 311/72; C07H 15/26
See application file for complete search history.

(56) References Cited

U.S. PATENT DOCUMENTS 5,102,895 A 4/1992 Hirose
5,280,111 A * 1/1994 Shoji ..................... A61K 31/70
536/18.1
9,695,209 B2 7/2017 Dauvergne
2010/0311956 A1 12/2010 Gellman
2019/0169218 A1 6/2019 Chae et al.

FOREIGN PATENT DOCUMENTS

| JP | 2001-262192 | 9/2001 |
| KR | 10-2017-0117894 | 10/2017 |
| WO | WO 2019/088374 | 5/2019 |

OTHER PUBLICATIONS

International Search Report and Written Opinion dated Aug. 1, 2018 From the International Searching Authority Re. Application No. PCT/KR2018/002462 and Its Translation of Search Report Into English. (10 Pages).
Newstead et al. "Insights Into Outer Membrane Protein Crystallization", Molecular Membrane Biology, 25(8): 631-638, Dec. 2008.
Newstead et al. "Rationalizing Alpha-Helical Membrane Protein Crystallization", Protein Science, 17(3): 466-472, Published Online Jan. 24, 2008.

* cited by examiner

Primary Examiner — Matthew P Coughlin

(57) ABSTRACT

The present invention relates to a vitamin E-based amphipathic compound, a method for producing same, and a method for extracting, solubilizing, stabilizing, or crystallizing a membrane protein using same. By using a compound according to the present invention, not only is an excellent membrane protein extraction and solubilization effect achieved, but the membrane protein can be stably stored for a long period of time in an aqueous solution, and thus the compound can be utilized in analyzing the function and structure of the membrane protein. Moreover, the vitamin E-based amphipathic compounds exhibited superb properties in the visualization of protein compounds through an electron microscope. Membrane protein structure and function analysis is one of the fields of greatest interest in biology and chemistry today, and since at least half of new drugs currently being developed target membrane proteins, the vitamin E-based amphipathic compounds may be applied to the membrane protein structure research, which is closely related to the development of new drugs.

17 Claims, 13 Drawing Sheets

[FIG. 1]
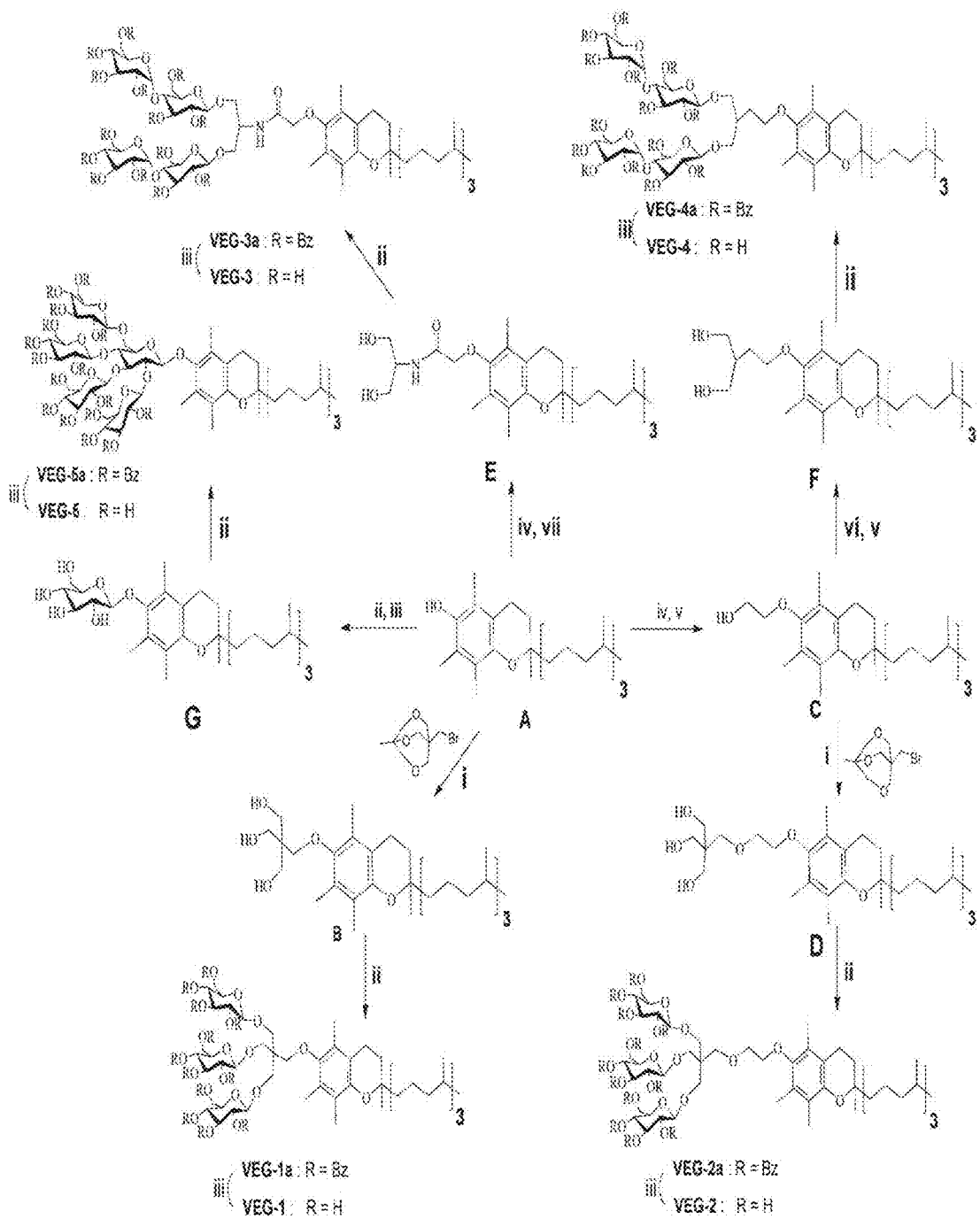

[FIG 2]
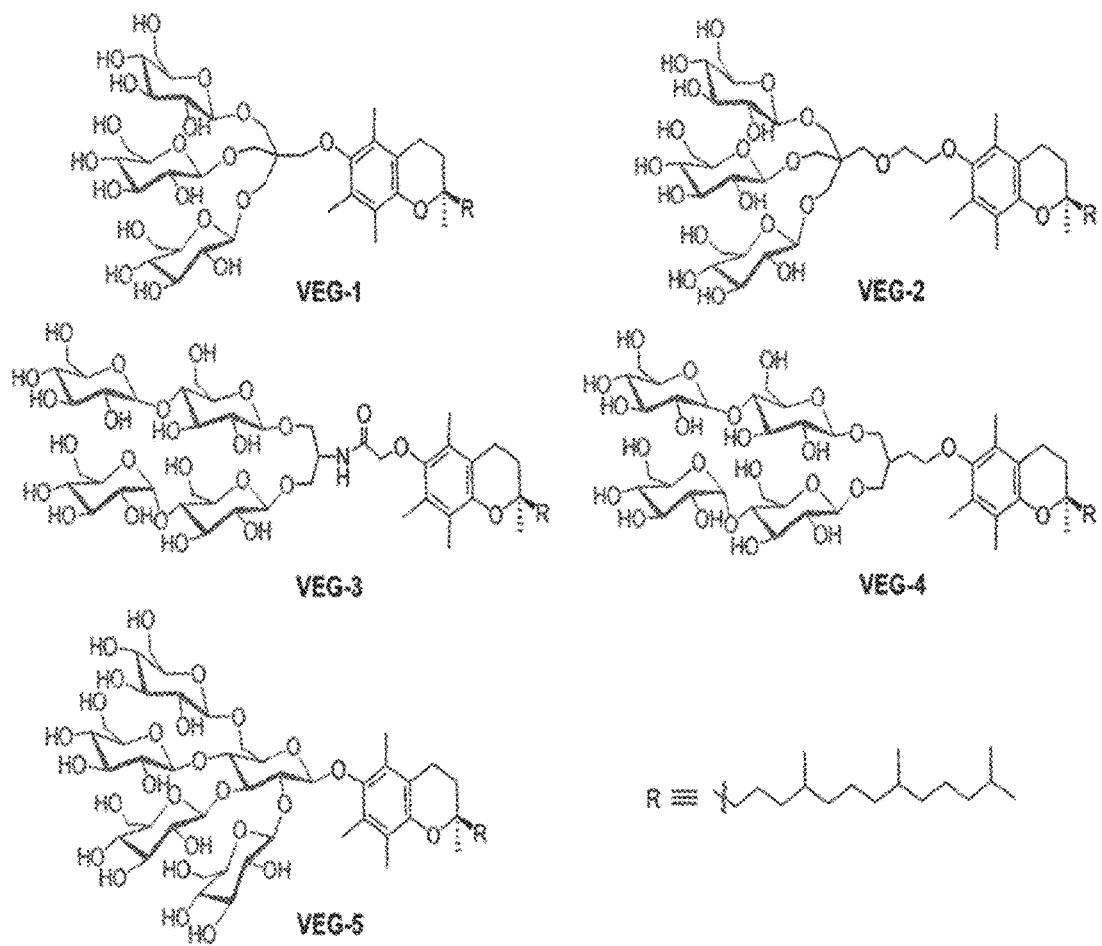

[FIG 3]
a
b
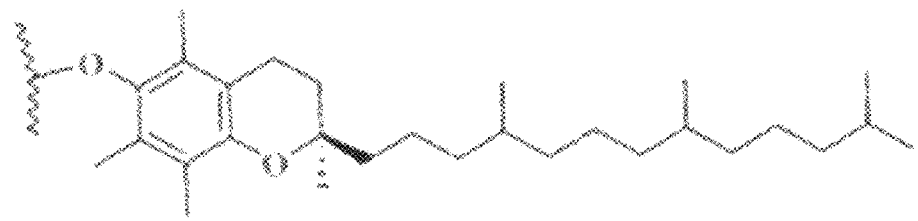
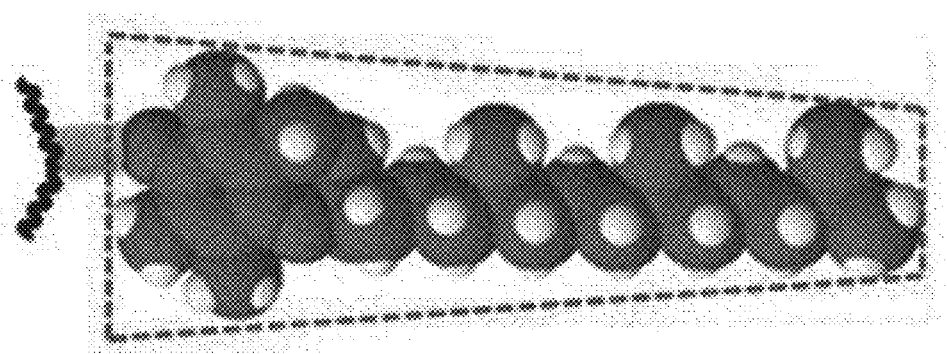

[FIG 4]
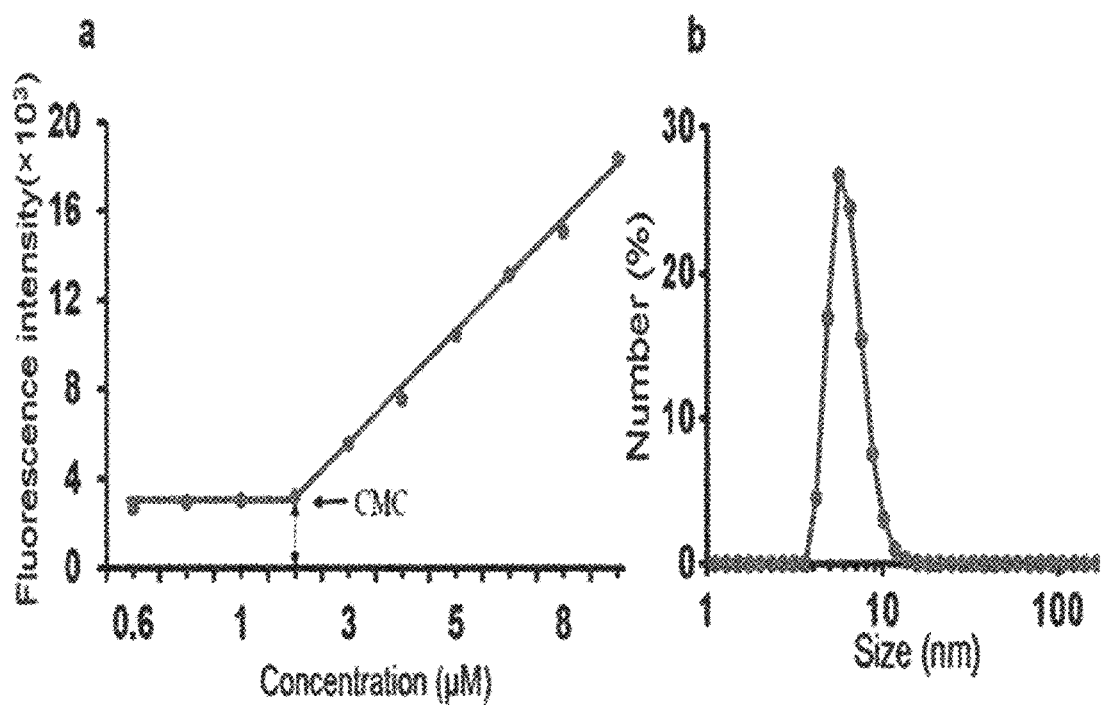

[FIG 5]
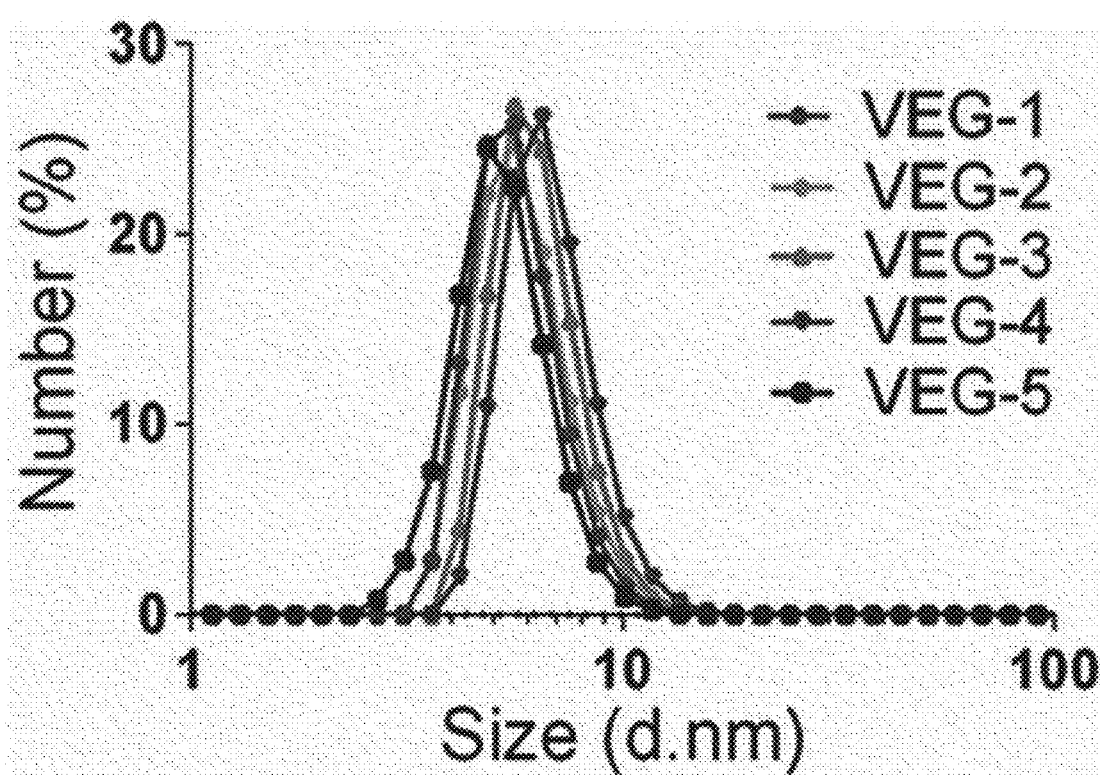

[FIG 6]
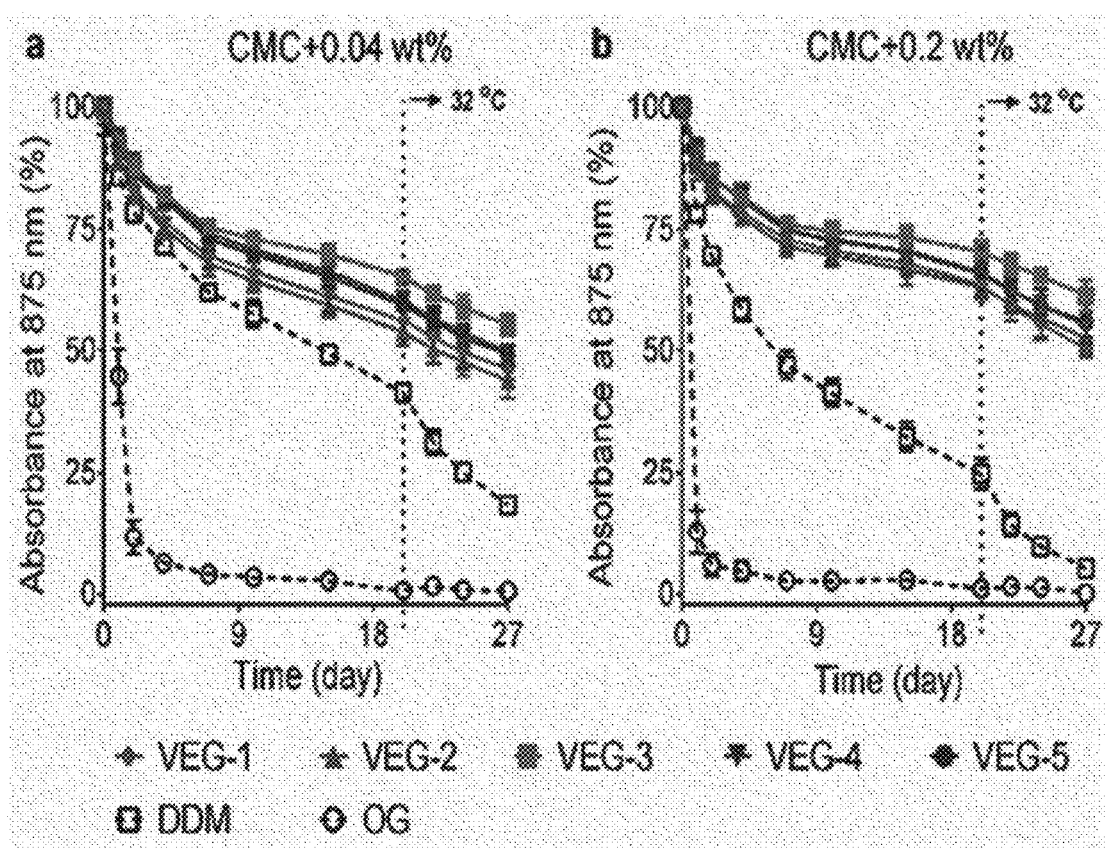

[FIG 7]
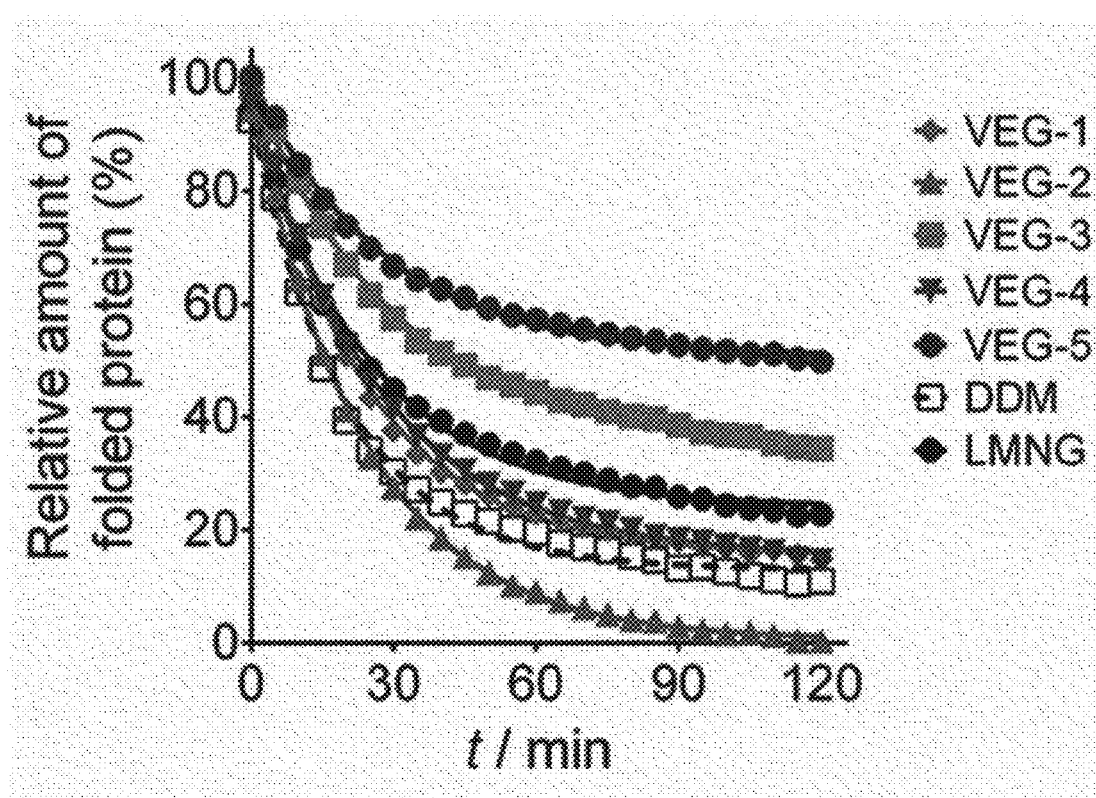

[FIG 8]
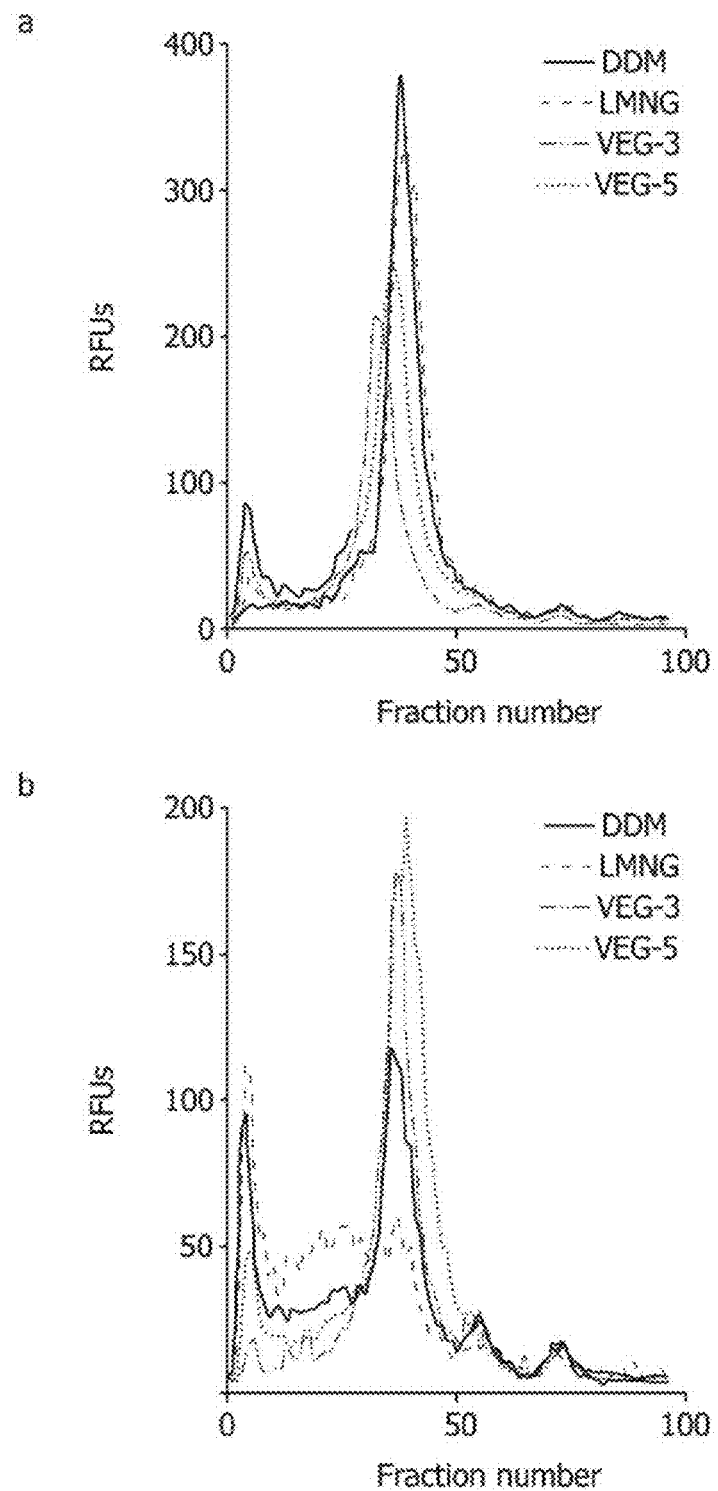

[FIG 9]
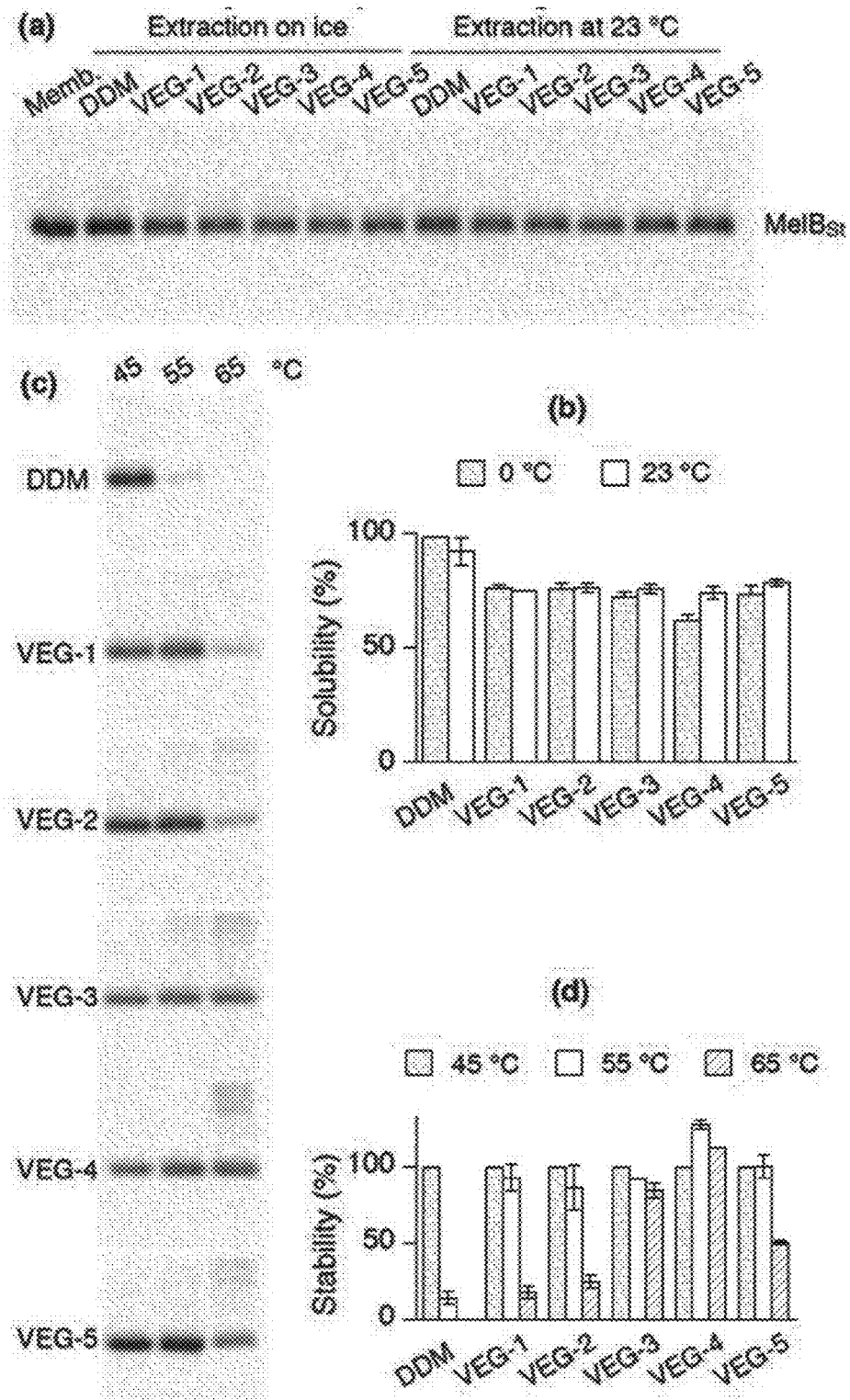

[FIG 10]
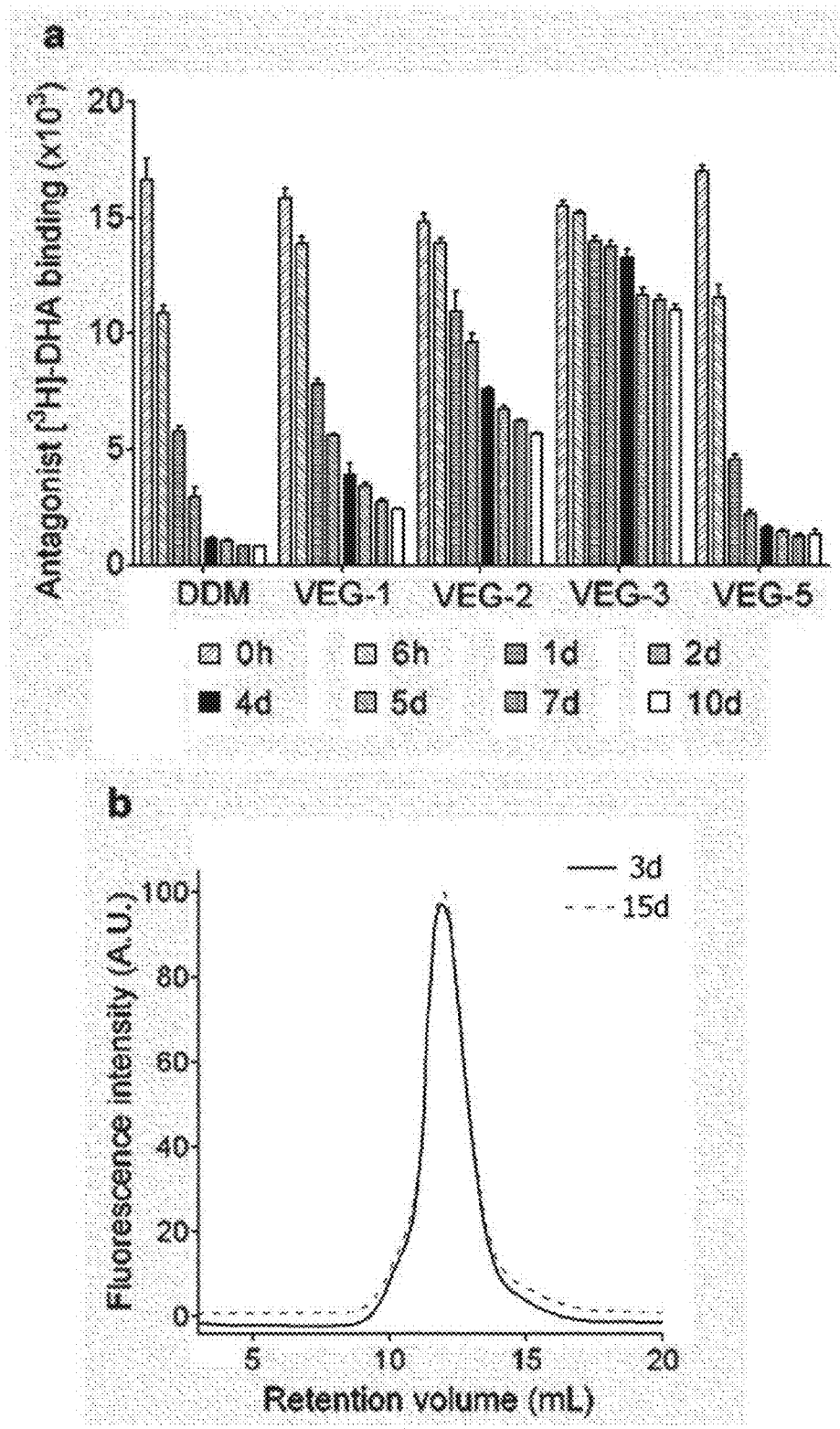

[FIG 11]
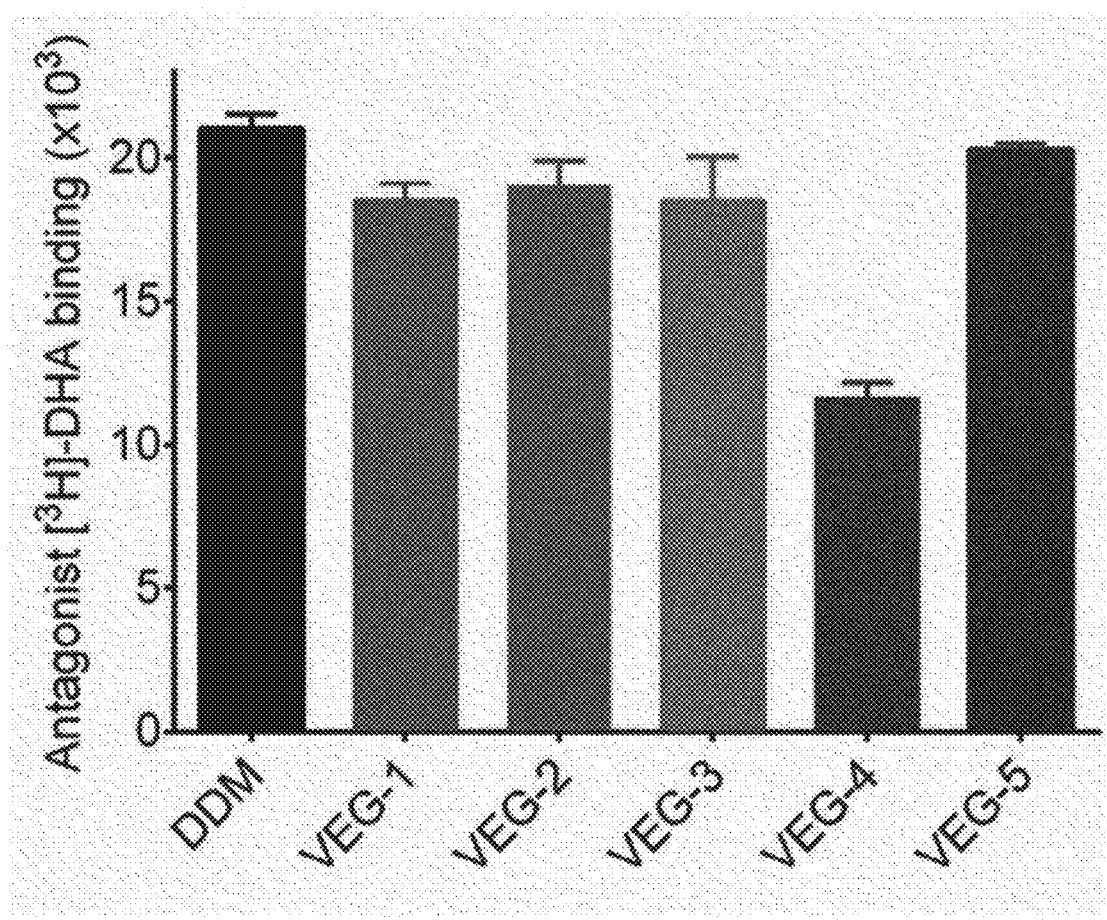

[FIG 12]
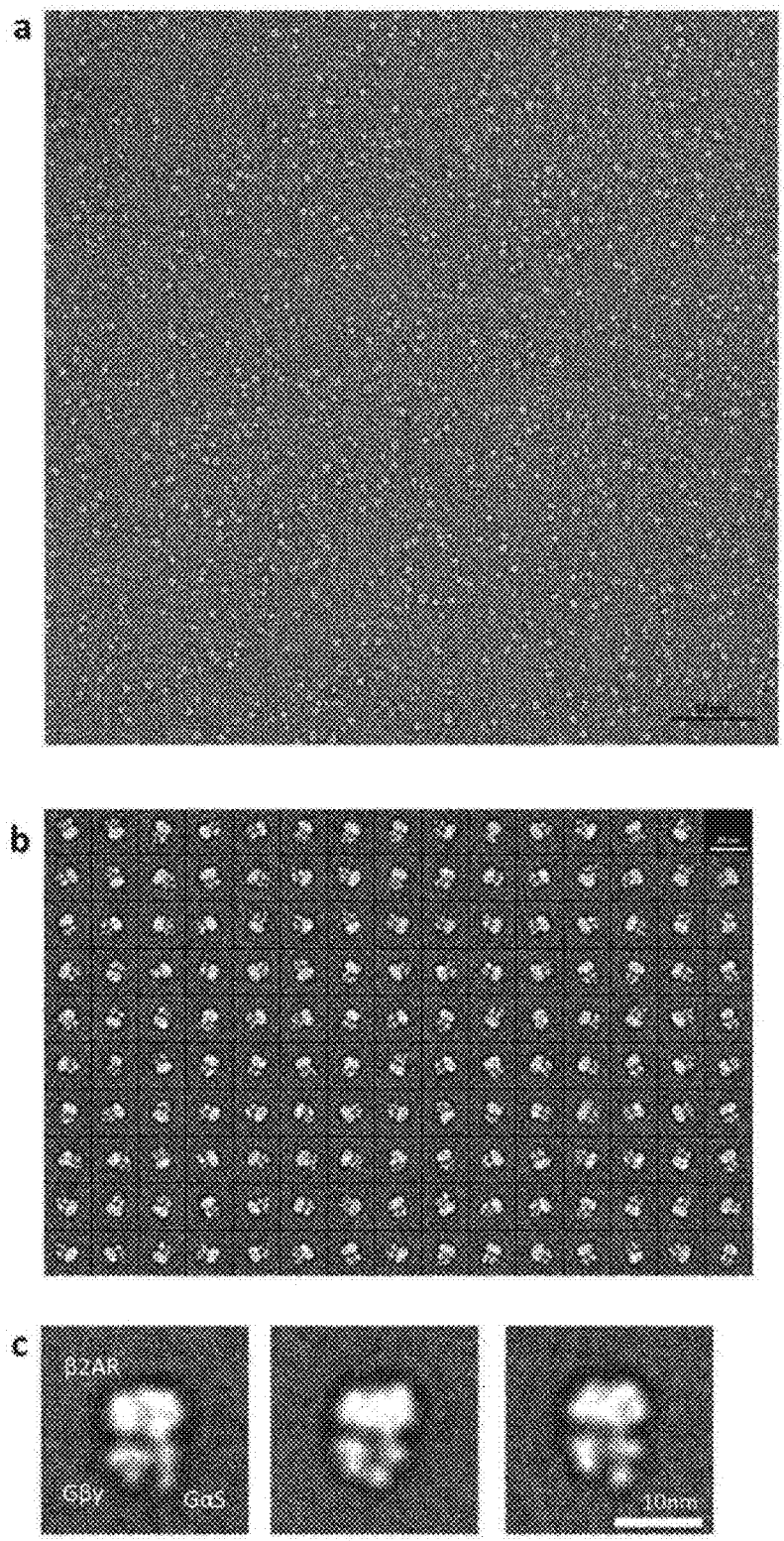

[FIG 13]
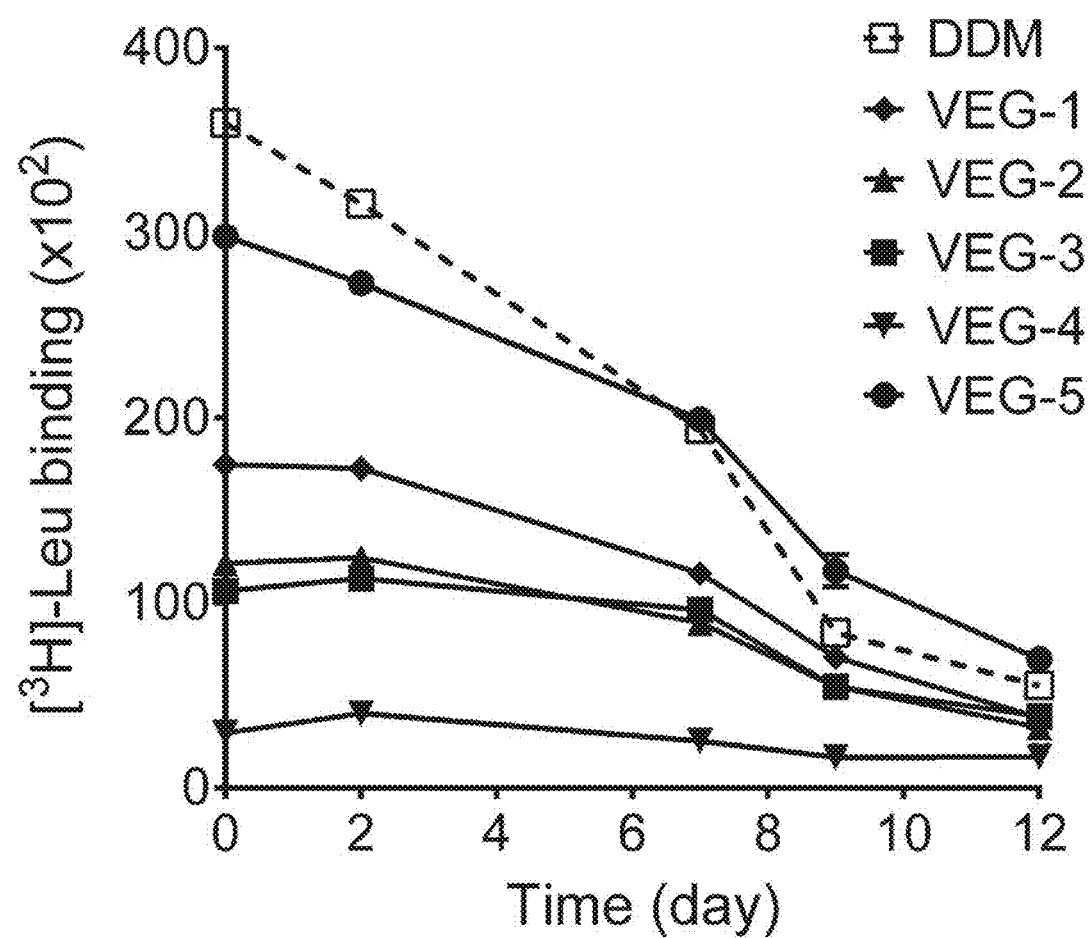

VITAMIN E-BASED AMPHIPATHIC COMPOUND, AND USE THEREOF

RELATED APPLICATIONS

This application is a National Phase of PCT Patent Application No. PCT/KR2018/002462 having International filing date of Feb. 28, 2018, which claims the benefit of priority of Korean Patent Application No. 10-2017-0144694 filed on Nov. 1, 2017.

FIELD AND BACKGROUND OF THE INVENTION

The present invention relates to a newly-developed vitamin E-based amphipathic compound and a method of extracting, solubilizing, stabilizing, crystallizing or analyzing a membrane protein using the same.

Membrane proteins play a pivotal role in a biological system. Since these bio-macromolecules include hydrophilic and hydrophobic moieties, amphiphilic molecules are required for extraction of membrane proteins from a lipid environment, and solubilization and stabilization of the membrane proteins in an aqueous solution.

To analyze the structure of a membrane protein, it is necessary to obtain a high quality of membrane protein crystals, and to this end, structural stability of the membrane protein in an aqueous solution should be preceded. Although there are 100 or more types of conventional amphiphilic molecules that have been used in membrane protein studies, only five of them are actively used for the membrane protein structure studies. These five types of amphoteric molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (Non-Patent Document 1, Non-Patent Document 2). However, since a lot of membrane proteins surrounded by these molecules are changed in structure, for example, easily denatured or aggregated, leading to rapidly losing their functions, there are a lot of limits on the research on the function and structure of a membrane protein using these molecules. This is because conventional molecules do not exhibit sufficiently diverse properties due to their simple chemical structures.

To analyze the structure of a membrane protein, maintenance of the structural stability of a membrane protein in an aqueous solution s important, and since there are still many unknown types of membrane proteins, and they have diverse structural properties, the number of membrane proteins that can be identified with the conventionally used amphiphilic molecules has been limited.

To solve the above-described problems, various amphipathic molecules have been developed, but currently, there are few examples using a natural substance as a hydrophobic group.

For this reason, the inventors had developed a novel amphipathic molecule containing a natural substance, vitamin E, as a hydrophobic group, and thus the present invention was completed.

(Non-Patent Document 1) S. Newstead et al., *Protein Sci.* 17 (2008) 466-472.
(Non-Patent Document 2) S. Newstead et al., *Mol. Membr. Biol.* 25 (2008) 631-638.

SUMMARY OF THE INVENTION

The present invention is directed to providing a compound represented by Formula 1 or 2.

The present invention is also directed to providing a composition for extracting, solubilizing, stabilizing, crystallizing or analyzing a membrane protein containing the compound.

The present invention is also directed to providing a method of preparing the compound.

The present invention is also directed to providing a method of extracting, solubilizing, stabilizing, crystallizing or analyzing a membrane protein using the compound.

One aspect of the present invention provides a compound represented by Formula 1 or 2 below:

[Formula 1]

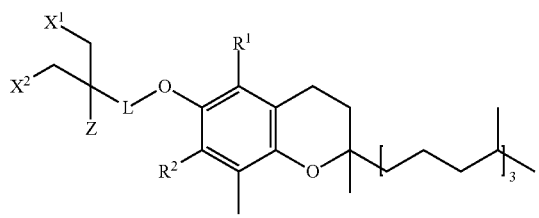

In Formula 1,
$R^1$ and $R^2$ may be each independently hydrogen (H) or $CH_3$;
L may be $-CH_2-$, $-CH_2CH_2-$, $NHCOCH_2-$, $-CH_2OCH_2CH_2-$ or a direct linkage;
$X^1$ and $X^2$ may be each independently an oxygen-linked saccharide;
Z may be hydrogen H) or $-CH_2-X^3$, and $X^3$ may be an oxygen-linked saccharide.

[Formula 2]

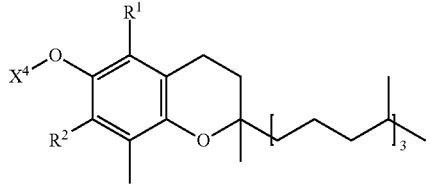

In Formula 2,
$R^1$ and $R^2$ may be each independently hydrogen (H) or $CH_3$; and
$X^4$ may be a glucose-centered, branched pentasaccharide.

The term "saccharide" used herein refers to a compound that has a relatively small molecule, compared with other carbohydrates, is dissolved in water and has a sweet taste. Saccharides are classified into monosaccharides, disaccharides and polysaccharides according to the number of molecules constituting a saccharide.

The saccharide used in the embodiment may be a monosaccharide or disaccharide, preferably glucose or maltose, and more preferably, maltose, but the present invention is not limited thereto.

The saccharide may act as a hydrophilic group. As two or three glucose or maltose molecules are linked in parallel to a hydrophilic moiety or a glucose-centered, branched polysaccharide is prepared to not only increase the size of the hydrophilic groups but also minimize the increase in length, the size of a complex formed with the compound according to one embodiment of the present invention and a membrane protein becomes smaller.

In the compound of the present invention, the vitamin E structure ray serve as a hydrophobic group. The type of vitamin E may vary according to functional groups of $R^1$ and $R^2$. Preferably, the compound of the present invention is vitamin E (alpha-tocopherol), in which both of $R^1$ and $R^2$ are methyl groups.

Due to the presence of a bulky bicyclic ring at the head portion of an alkyl chain, unlike a general linear alkyl chain used in a conventional amphipathic molecule, vitamin E used as the hydrophobic group forms a conical geometric molecular structure, and such a structure may be more suitable for interaction between compounds and membrane proteins.

In the compound of the present invention, the hydrophobic group and a hydrophilic group may be linked by various linker structures, and linkers that maintain the rigidity of the center of the compound and sufficiently ensure the flexibility of an alkyl chain are introduced.

In an exemplary embodiment, $R^1$ and $R^2$ may be methyl groups; L may be —$CH_2$— or —$CH_2OCH_2CH_2$—; Z may be —$CH_2$—$X^3$; and $X^1$ and $X^2$ may be oxygen-linked glucose or maltose.

In an exemplary embodiment, $R^1$ and $R^2$ may be methyl groups; L may be —$CH_2CH_2$— or —$NHCOCH_2$—; Z may be hydrogen; and $X^1$ and $X^2$ may be oxygen-linked glucose or maltose.

In an embodiment of the present invention, the compound represented by Formula 1 or 2 is referred to as "vitamin E-based glycoside (VEG)."

More specifically, in an embodiment of the present invention, a compound in which $R^1$ and $R^2$ of Formula 1 may be methyl groups; L may be —$CH_2$— or —$CH_2$—$X^3$; and $X^1$ and $X^3$ may be oxygen-linked glucoses is referred to as "VEG-1," represented by Formula 3 below.

[Formula 3]

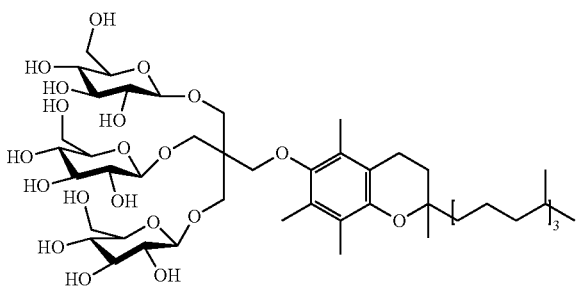

More specifically, in an embodiment of the present invention, a compound in which $R^1$ and $R^2$ of Formula 1 may be methyl groups; L may be —$CH_2OCH_2CH_2$—; Z may be —$CH_2$—$X^3$; and $X^1$ and $X^3$ may be oxygen-linked glucoses is referred to as "VEG-2," represented by Formula 4 below.

[Formula 4]

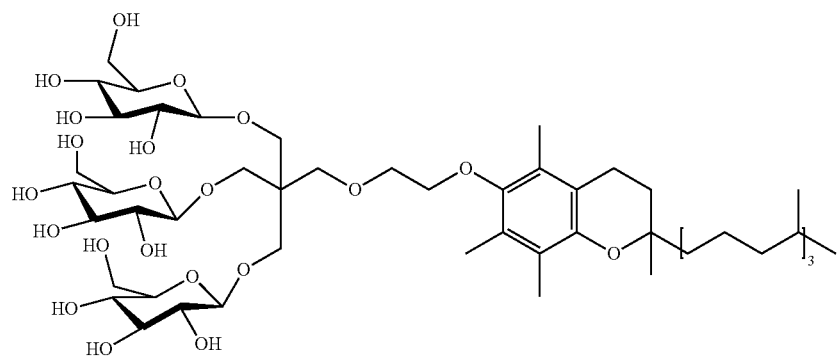

More specifically, in an embodiment of the present invention, a compound in which $R^1$ and $R^2$ of Formula 1 may be methyl groups; L may be —$NHCOCH_2$—; Z may be hydrogen; and $X^1$ and $X^2$ may be oxygen-linked maltoses is referred to as "VEG-3," represented by Formula 5 below

[Formula 5]

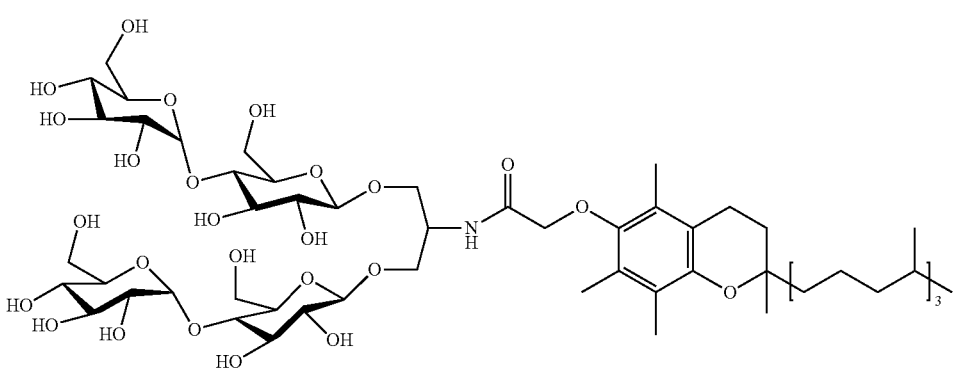

More specifically, in an embodiment of the present invention, a compound in which $R^1$ and $R^2$ of Formula 1 may be methyl groups; L may be —$CH_2CH_2$—; Z may be hydrogen; and $X^1$ and $X^2$ may be oxygen-linked maltoses is referred to as "VEG-4," represented by Formula 6 below.

[Formula 6]

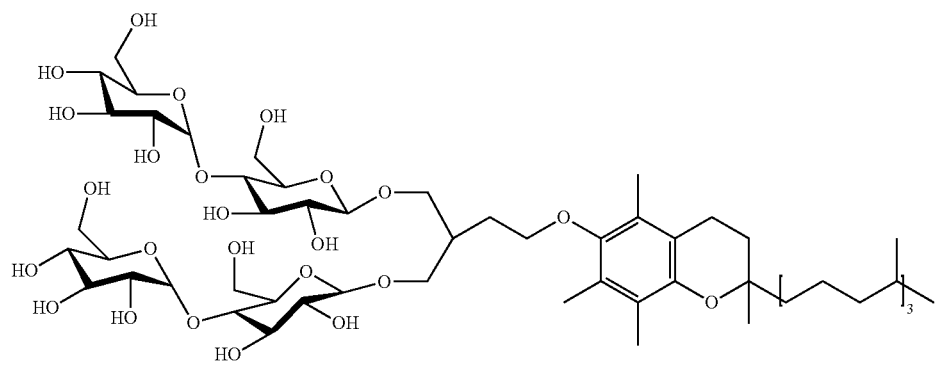

More specifically, in an embodiment of the present invention, a compound in which $R^1$ and $R^2$ of Formula 2 may be methyl groups; $X^4$ may be a glucose-centered, branched pentasaccharide is referred to as "VEG-5," represented by Formula 7 below.

[Formula 7]

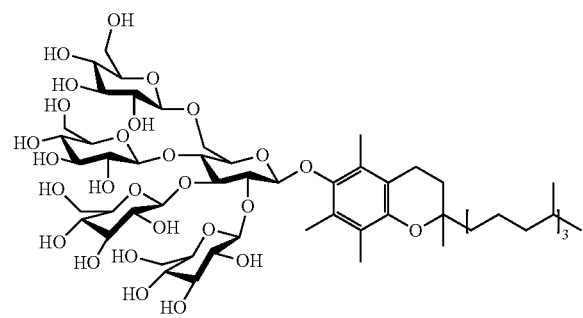

A compound according to another embodiment of the present invention nay be an amphipathic molecule for extracting, solubilizing, stabilizing, crystallizing or analyzing a membrane protein, but the present invention is not limited thereto.

The term "amphiphilic molecule" used herein refers to a molecule displaying the properties of polar and non-polar solvents because one molecule includes both of a hydrophobic group and a hydrophilic group. Phospholipid molecules present in a surfactant or cell membrane are molecules having a hydrophilic group at one end and a hydrophobic group at the other end, and are amphiphilic and form micelles or liposomes in an aqueous solution. Since the hydrophilic group has polarity, but the non-polar group is also present, the amphiphilic molecule is not well dissolved in water. However, when a concentration reaches a critical micelle concentration (CMC) or higher, due to a hydrophobic interaction, a micelle in which hydrophobic groups gather together, and hydrophilic groups are placed on its surface is produced, and thus solubility in water greatly increases.

A method of measuring CMC is not particularly limited, and may be a method widely known in the art, for example, fluorescent staining using diphenylhex riene (DPH).

The compound according to one embodiment of the present invention may have a CMC in an aqueous solution of 0.0001 mM to 1 mM, preferably, 0.0001 mM to 0.01 mM, and more preferably, 0.001 mM to 0.01 mM, but the present invention is not limited thereto.

DDM, which has been mainly used in conventional membrane protein studies, has a CMC of 0.17 mM, and VEGs of the embodiment have much smaller CMC values than DDM. Therefore, since VEGs easily form micelles even at a small amount, membrane proteins may be effectively studied and analyzed with a small amount, confirming that VEGs are advantageous over DDM.

Another aspect of the present invention provides a composition tor extracting, solubilizing, stabilizing, crystallizing or analyzing a membrane protein, which includes the compound.

The compound may be prepared in the form of a micelle, liposome, emulsion or nanoparticle, but the present invention is not limited thereto.

The micelle may have a radius of 2.0 to 30.0 nm, preferably 3.0 to 20.0 nm, and more preferably, micelles formed of VEGs according to embodiments of the present invention may have a radius of 3.0 to 5.0 nm, but the present inventions not limited thereto.

A method of measuring the radius of a micelle is not particularly limited, but may be a method well known in the art, for example, dynamic light scattering (DLS).

The micelle, liposome, emulsion or nanoparticle may contain a membrane protein. That is, the micelle, liposome, emulsion or nanoparticle may envelop a previously-extracted membrane protein present in the cell membrane. Therefore, the micelle can be used to extract, solubilize, stabilize, crystallize or analyze a membrane protein.

The composition may further include a buffer that can help in extracting, solubilizing, stabilizing or analyzing a membrane protein.

In addition, still another aspect of the present invention provides a method of preparing a compound represented by Formula 1 below, which includes Steps 1) to 4) below:

1) introducing a linker having a —$CH_2$—, —$CH_2CH_2$—, $NHCOCH_2$—$CH_2OCH_2CH_2$— structure to vitamin E (tocopherol);

2) producing an alcohol group by reacting the product of Step 1) with 4-(bromomethyl)-methyl-2,6,7-trioxabicyclo[2,2,2]-octane or diethyl malonate and performing reduction;

3) introducing a protecting group-attached saccharide by performing glycosylation on the product of Step 2); and 4) performing deprotection on the product of Step 3).

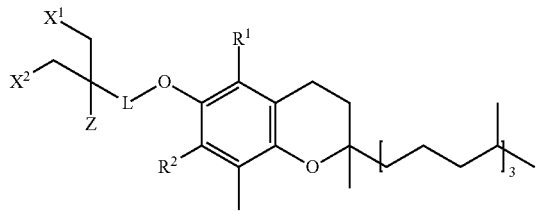

[Formula 1]

in Formula 1, $R^1$ and $R^2$ may be each independently hydrogen (H) or $CH_3$;

L may be $—CH_2—$, $—CH_2CH_2—$, $NHCOCH_2—$, $—CH_2OCH_2CH_2—$ or a direct linkage;

$X^1$ and $X^2$ may be each independently an oxygen-linked saccharide; and

Z may be hydrogen (H) or and $—CH_2—X^3$ may be an oxygen-linked saccharide.

Compounds prepared by the method may be compounds represented by Formulas 3 to 6.

In addition, yet another aspect of the present invention provides a method of preparing a compound represented by Formula 2 below, including Steps 1) to 4) below:

1) introducing a protecting group-attached saccharide by performing glycosylation on vitamin E (tocopherol);

2) performing deprotection on the product of Step 1); and 3) the reactions of 1) and 2) are repeatedly performed.

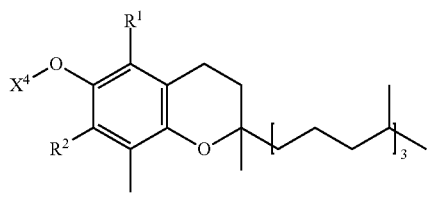

[Formula 2]

In Formula 2, $R^1$ and $R^2$ may be each independently hydrogen (H) or $CH_3$; and $X^4$ max be a glucose-centered, branched pentasaccharide.

The compound prepared according to the method may be a compound represented by Formula 7.

In addition, yet another aspect of the present invention provides a method of extracting, solubilizing, stabilizing, crystallizing or analyzing a membrane protein. Specifically, a method of extracting, solubilizing, stabilizing, crystallizing or analyzing a membrane protein, which includes treating a membrane protein with a compound represented by Formula 1 or 2 below in an aqueous solution:

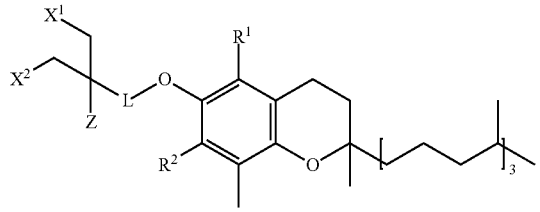

[Formula 1]

In Formula 1, $R^1$ and $R^2$ may be each independently hydrogen (H) or $CH_3$;

L may be $—CH_2—$, $—CH_2CH_2—$, $NHCOCH_2—$, $—CH_2OCH_2CH_2—$ or a direct linkage;

$X^1$ and $X^2$ may be each independently an oxygen-linked saccharide; and

Z may be hydrogen (H) or $—CH_2—X^3$, and $X^3$ may be an oxygen-linked saccharide,

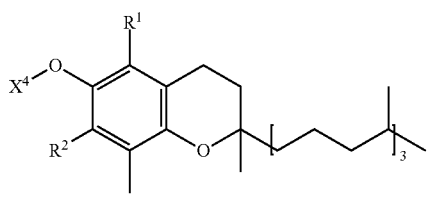

[Formula 2]

In Formula 2, $R^1$ and $R^2$ may be each independently hydrogen (H) or $CH_3$; and $X^4$ may be a glucose-centered, branched pentasaccharide.

In an exemplary embodiment, $R^1$ and $R^2$ may be methyl groups; L may be $—CH_2—$ or $—CH_2OCH_2CH_2—$; Z nmy be $—CH_2—X^3$; and $X^1$ and $X^2$ may be oxygen-linked glucose or maltose.

In an exemplary embodiment, $R^1$ and $R^2$ may be methyl groups; L may be $—CH_2CH_2—$ or $—NHCOCH_2—$; Z may be hydrogen; and $X^1$ and $X^2$ may be oxygen-linked glucose or maltose.

The compounds may be 5 types of compounds represented by Formula 3 to 7 according to an embodiment of the present invention, but the present invention is not limited thereto.

The term "membrane protein" is the collective term for proteins or glycoproteins that penetrate or are associated with the cell membrane lipid bilayer. These proteins may be present in various states, for example, may pass through the entire layers of the cell membrane, may be located on the surface layer, or may be transiently associated with the cell membrane. Examples of the membrane proteins may include, but are not limited to, receptors for enzymes, peptide hormones, local hormones, etc., hydrophilic carriers for sugars, ion channels, cell membrane antigens, etc.

The membrane protein includes any protein or glycoprotein that penetrates or is associated with the cell membrane lipid bilayer, and preferably, a complex of light harvesting-I and a reaction center (LHI-RC complex), a uric acid-xanthine/H$^+$ symporter (UapA), melibiose permease (MelB), a leucine transporter (LeuT), a G-protein coupled receptor (GPCR) or a combination of two or more thereof, but the present invention is not limited thereto.

The term "extraction of a membrane protein" refers to isolation of a membrane protein from the cell membrane.

The term "solubilization of a membrane protein" refers to dissolving a membrane protein which is not soluble in water in a micelle n an aqueous solution.

The to "stabilization of a membrane protein" refers to stable conservation of a tertiary or quaternary structure to prevent the structure and function of a membrane protein from being changed.

The term "crystallization of a membrane protein" refers to formation of a membrane protein crystal in a solution.

The ter "analysis of a membrane protein" refers to analysis of the structure or function of a membrane protein. In the embodiment, the analysis of a membrane protein may be performed by a known method, and the structure of a membrane protein may be analyzed by electron microscopy, but the present invention is not limited thereto.

When an amphiphilic compound containing vitamin E as a hydrophobic group according to an embodiment of the present invention is used, compared with a conventional compound, a membrane protein can be more stably stored in an aqueous solution for a longer time, and the compound of the present invention can be used in the functional and structural analyses of the membrane protein.

The functional and structural analyses of a membrane protein are one of the most popular fields in biology and chemistry, and since more than half of the novel drugs currently being developed target membrane proteins, the compound of the present invention can be applied in research of a protein structure closely associated with drug development.

BRIEF DESCRIPTION OF THE SEVERAL VIEWS OF THE DRAWINGS

FIG. 1 shows the synthetic scheme for VEGs of the present invention.

FIG. 2 shows the chemical structures of VEGs of the present invention.

FIG. 3 shows the result of comparing (a) an alkyl chain structure of a hydrophobic moiety (DDM) of an amphipathic molecule and (h) a vitamin E structure of VEG in terms of a molecular geometry aspect.

FIG. 4 shows a set of dynamic light scattering (DLS) profiles of micelles formed by individual VEGs.

FIG. 5 is a graph showing the physical properties of VEG-3 self-assemblies.

FIG. 6 is a set of graphs showing the structural stability of an LHI-RC complex solubilized by VEGs used at (a) CMC+0.04 wt % and (b) CMC+0.2 wt %, respectively, measured by monitoring absorbance at 875 nm at regular intervals.

FIG. 7 is a graph showing UapA thermal stability in an aqueous solution by VEGs or DDM at the final concentration of CMC+0.2 wt %, measured by CPM assay:

FIG. 8 shows the results of evaluating the thermal stability of UapA solubilized by VEGs (VEG-3 and VEG-5), DDM or LMNG, compared by fluorescence size exclusion chromatography (FSEC) (a) before thermal treatment and (b) after thermal treatment.

FIG. 9 shows the result of measuring the amounts of MelB$_{st}$ protein dissolved in an aqueous solution, following the extraction of MelB$_{st}$ protein for 90 minutes at two different temperature (0 and 23° C.), and incubation of protein samples extracted at 23° C. for 90 minutes at three different temperatures (45, 55, and 65° C.), using 1.5 wt % VEGs or DDM:

(a) and (c) show SDS-PAGE and Western blotting results for assessing the amounts of MelB$_{st}$ protein dissolved in the presence of each amphipathic compound; and (b) and (d) show a histogram expressed as percentages (%) of the total amount of MelB$_{st}$ protein present in a solution prepared by thermally treating the amounts of MelB$_{st}$ protein dissolved in the presence of individual amphipathic compounds at 45° C.

FIG. 10 is a set of graphs showing (a) the long-term stability of β$_2$AR solubilized in DDM and VEGs and (b) the long-term SEC profiles of a β$_2$AR-G$_s$ complex in VEG-3.

FIG. 11 shows the stability of β$_2$AR solubilized in DDM and VEGs, which was assessed by measuring protein activity using [$^3$H]-dihydroalprenolol (DI-IA), following incubation of β$_2$AR solubilized in CMC+0.2 wt to DDM and VEGs at room temperature for 30 minutes.

FIG. 12 shows the EM analysis results for a β$_2$AR-G$_s$ complex solubilized in VEG-3.

FIG. 13 is a graph showing the result obtained by scintillation proximity assay (SPA) to assess the long-term stability of a LeuT protein solubilized by VEGs at a concentration of CMC+0.04 wt %.

DESCRIPTION OF SPECIFIC EMBODIMENTS OF THE INVENTION

Hereinafter, the present invention will be described in detail with reference to the following examples. However, the following examples are merely provided to exemplify the contents of the present invention, and do not limit the scope of the present invention. It will be interpreted that what can be easily inferred from the detailed description and examples of the present invention by those of ordinary skill in the art is within the scope of the present invention.

<Preparation Example 1> Method of Synthesizing VEG-1

The synthetic scheme for VEG-1 is shown in FIG. 1. The VEG-1 compound was synthesized according to a synthetic method including Steps <1-1> to <1-3> below, and is shown in FIG. 2.

<1-1> Synthesis of Compound B of FIG. 1

A mixture of vitamin E (Compound A; DL-α-tocopherol, 1.0 equiv.) was treated with NaH (3.0 equiv.) mixed with DMF (12 mL), and the reaction mixture was stirred vigorously for 15 minutes at room temperature. 4-(bromo ethyl)-ethyl-2,6,7-trioxabicyclo[2,2,2]-octane (1.8 equiv.) dissolved in TI-IF (12 mL) was added dropwise to the reaction mixture. The resulting mixture was heated under nitrogen for 24 hours at 100° C. After the reaction was quenched with methanol, an organic solvent was removed under reduced pressure. The solid residue was dissolved in CH$_2$Cl$_2$, and an organic solution was washed with brine and dried over anhydrous Na$_2$SO$_4$. An organic solvent was concentrated, and then the residue was dissolved in a CH$_2$Cl$_2$/MeOH mixture. Several drops of concentrated HCl were added to this solution. The resulting mixture was heated for 4 hours at 50° C. Following neutralization with NaOH and concentration of the reaction mixture, the residue was purified by column chromatography (EtOAc/hexane), obtaining desired Compound B in 78% yield.

$^1$H NMR (400 MHz, CDCl$_3$): δ 3.92 (s, 6H), 3.66 (s, 2H), 3.05 (br s, 3H), 2.56 (t, J=6.8 Hz, 2H), 2.16 (s, 3H), 2.12 (s, 3H), 2.07 (s, 3H), 1.88-1.72 (m, 2H), 1.54-1.50 (m, 3H), 1.43-1.05 (m, 21H), 0.88-0.84 (m, 12H); $^{13}$C NMR (100

MHz, CDCl$_3$): δ 148.4, 147.1, 127.7, 125.8, 123.4, 118.0, 75.1, 64.8, 45.4, 40.2, 40.1, 39.6, 37.7, 37.6, 37.5, 32.9, 32.8, 31.4, 28.1, 25.0, 24.6, 24.0, 22.9, 22.8, 21.3, 20.8, 19.9, 19.8, 12.8, 12.0, 11.9.

<1-2> Synthesis of VEG-1a Through General Procedure for Glycosylation

Under a N$_2$ atmosphere, a mixture of Compound 13 (1.0 equiv.), AgOTf (3.6 equiv.) and 2,4,6-collidine (1.0 equiv.) in anhydrous CH$_2$Cl$_2$ was stirred at −45° C. A solution of perbenzoylated maltosylbromide (3.6 equiv.) mixed with CH$_2$Cl$_2$ was added dropwise to the resulting suspension. After stirring for 30 minutes at −45° C., the reaction mixture was heated to 0° C. and stirred for 30 minutes. After the completion of the reaction (indicated by TLC), pyridine was added to the reaction mixture, followed by dilution with CH$_2$Cl$_2$ and filtration over Celite. The resulting filtrate was washed sequentially with a 1M Na$_2$S$_2$O$_3$ aqueous solution, a 0.1M HCl aqueous solution and brine. An organic layer was dried with anhydrous Na$_2$SO$_4$, and the solvent was removed by a rotary evaporator. The residue was purified by silica gel column chromatography (EtOAc/hexane), obtaining VEG-1a as a glassy solid in 80% yield.

$^1$H NMR (400 MHz, CDCl$_3$): δ 8.10-7.83 (m, 7.62-7.15 (m, 42H), 5.66 (t, =9.6 Hz, 3H), 5.56 (t, =9.6 Hz, 3H), 5.41 (t, =8.0 Hz, 3H), 4.42-4.39 (m, 3H), 4.33-4.30 (m, 3H), 4.12 (d, J=8.0 Hz, 3H), 4.02 (d, J=8.0 Hz, 3H), 3.73 (d, J=8.0 Hz, 1H), 3.54 (d, J=8.0 Hz, 1H), 3.34 (m, 6H), 2.56 (t, J=6.8 Hz, 2H), 2.16 (s, 3H), 2.12 (s, 3H), 2.07 (s, 3H), 1.88-1.72 (m, 2H), 1.54-1.50 (m, 3H), 1.43-1.05 (m, 21H), 0.88-0.84 (m, 12H); $^{13}$C NMR (100 MHz, CDCl$_3$): δ 166.1, 165.9, 165.1, 164.7, 147.7, 147.3, 133.6, 133.5, 133.3, 133.1, 130.0, 129.8, 129.6, 129.1, 128.9, 128.8, 128.6, 128.5, 128.4, 128.1, 126.1, 122.5, 117.3, 101.23, 74.6, 72.6, 71.9, 71.8, 69.5, 68.1, 62.9, 45.0, 39.4, 37.7, 37.5, 37.4, 32.8, 28.0, 24.9, 24.5, 23.8, 22.8, 22.7, 21.2, 19.9, 12.45, 11.8, 12.4, 11.8, 11.6.

<1-3> Synthesis of VEG-1 Through Deprotection

O-benzoylated VEG-1a was dissolved in MeOH and treated with a required amount of a methanol solution of 0.5M NaOMe, such that the final concentration of NaOMe was 0.05M. The reaction mixture was stirred for 6 hours at room temperature, and neutralized with Amberlite IR-120 (H$^+$ form). The resin was removed by filtration and washed with MeOH, and a solvent was removed from the combined filtrate in vacuo. 50 mL of diethyl ether was added to the residue dissolved in a 2 mL MeOH:CH$_2$Cl$_2$ (1:1) mixture, obtaining VEG-1 as a white solid in 92% yield.

$^1$H NMR (400 MHz, CD$_3$OD): δ 4.33 (d, J=8.0 Hz, 3H), 4.17 (d, J=8.0 Hz, 3H), 3.83-3.74 (m, 8H), 3.61-3.59 (m, 5H), 3.34 (t, J=8.0 Hz, 3H), 3.25-3.22 (m, 8H), 3.17 (t, J=8.0 Hz, 4H), 2.50 (t, J=8.0 Hz, 2H), 2.11 (s, 3H), 2.07 (s, 3H), 1.97 (s, 3H), 1.71-1.66 (m, 2H), 1.49-1.32 (m, 8H), 1.24-1.21 (m, 8H), 1.13-1.04 (m, 11H), 0.82-0.79 (m, 12H); $^{13}$C NMR (100 MHz, CD$_3$OD): δ 149.0, 148.9, 129.14, 127.3, 123.7, 118.7, 104.8, 78.0, 77.8, 75.7, 75.3, 72.9, 71.8, 70.0, 62.9, 46.6, 41.0, 40.6, 38.8, 38.7, 38.6, 38.5, 38.4, 34.0, 33.9, 33.8, 32.7, 29.2, 26.0, 25.5, 24.2, 24.1, 23.3, 23.2, 22.1, 21.7, 20.4, 20.3, 13.4, 12.5, 12.2; HRMS (FAB*); calcd. for C$_{52}$H$_{90}$O$_{20}$[M+Na]$^+$ 1057.5923, observed 1057.5920.

<Preparation Example 2> Synthesis of VEG-2

The synthetic scheme for VEG-2 is shown in FIG. 1. The VEG-2 compound was synthesized according to a synthetic method including Steps <2-1> to <2-4> below, and is shown in FIG. 2.

<2-1> Synthesis of Compound C of FIG. 1

A mixture of vitamin E (Compound A; DL-α-tocopherol, 16 mmol), methyl bromoacetate (22 mmol), anhydrous K$_2$CO$_3$ (35 mmol) and KI (8 mmol) in anhydrous acetone was stirred under an argon atmosphere to reflux overnight. After the removal of a solvent, the residue was dissolved in CH$_2$Cl$_2$, and extracted with water and brine. An organic layer was dried over anhydrous Na$_2$SO$_4$, filtered, and concentrated under reduced pressure. After complete removal of a solvent, LiAlH$_4$ (14.0 mmol) was slowly added to the residue dissolved in THF at 0° C. The mixture was stirred for 4 hours at room temperature, and the reaction was quenched by sequentially adding MeOH, water and a 1.0N HCl aqueous solution at 0° C., followed by extraction with CH$_2$Cl$_2$ twice. Combined organic layers were washed with brine, and dried over anhydrous Na$_2$SO$_4$. The residue was purified by silica gel column chromatography (EtOAc/hexane), obtaining desired Compound C in 85% yield.

$^1$H NMR (400 MHz, CDCl$_3$): δ 3.92-3.90 (m, 2H), 3.77-3.75 (m, 2H), 2.75 (br s, 1H), 2.57 (t, =6.8 Hz, 2H), 2.17 (s, 3H), 2.13 (s, 3H), 2.08 (5, 3H), 1.88-1.72 (m, 2H), 1.54-1.50 (m, 3H), 1.43-1.05 (m, 21H), 0.88-0.84 (m, 12H); $^{13}$C NMR (100 MHz, CDCl$_3$): δ 148.1, 147.7, 127.8, 125.8, 123.0, 117.0, 74.9, 73.9, 62.4, 53.5, 40.3, 40.2, 39.5, 37.8, 37.7, 37.6, 37.5, 37.4, 33.0, 32.9, 32.8, 31.4, 31.3, 28.1, 25.0, 24.9, 24.6, 24.0, 22.9, 22.8, 21.2, 20.8, 19.9, 19.6, 12.8, 11.9.

<2-2> Synthesis of Compound D of FIG. 1

Compound C was treated with NaH (3.0 equiv.) mixed with DMF (12 mL), and the react on as stirred vigorously for 15 minutes at room temperature. 4-(bromoethyl)-ethyl-2,6,7-trioxabicyclo[2,2,2]-octane (1.8 equiv.) dissolved in THF (12 mL) was added dropwise to the reaction mixture. The resulting mixture was heated under nitrogen for 24 hours at 100° C. After the reaction was quenched with methanol, an organic solvent was removed under reduced pressure. The solid residue was dissolved in CH$_2$Cl$_2$, and an organic solvent was washed with brine and dried over anhydrous Na$_2$SO$_4$. After concentration of an organic solvent, the residue was dissolved in a CH$_2$Cl$_2$/MeOH mixture. Several drops of concentrated HCl were added to the solution. The resulting mixture was heated for 4 hours at 50° C. After neutralization with NaOH and concentration of the reaction mixture, the residue was purified by column chromatography (EtOAc/hexane obtaining desired Compound D in 80% yield.

$^1$H NMR (400 MHz, CDCl$_3$): δ 3.78-3.76 (m, 2H), 3.70 (s, 6H), 3.60 (s, 2H), 3.50 (s, 2H), 2.55 (t, J=6.8 Hz, 2H), 2.15 (s, 3H), 2.11 (s, 3H), 2.06 (s, 3H), 1.88-1.72 (m, 2H), 1.54-1.50 (m, 3H), 1.43-1.05 (m, 21H), 0.87-0.83 (in, 12H); $^{13}$C NMR (100 MHz, CDCl$_3$): δ 148.1, 147.7, 127.8, 125.9, 123.1, 117.8, 75.0, 73.1, 72.0, 71.2, 64.1, 45.4, 40.4, 40.3, 39.5, 37.7, 37.6, 37.5, 37.4, 33.0, 32.9, 32.8, 31.4, 31.3, 28.1, 25.0, 24.9, 24.6, 24.0, 22.9, 22.8, 21.2, 20.8, 20.0, 19.9, 19.8, 19.7, 19.6, 12.8, 11.9.

<2-3> Synthesis of VEG-2a through general procedure for glycosylation

Under a N$_2$ atmosphere, a mixture of Compound D (1.0 equiv.), AgOTf (3.6 equiv.) and 2,4,6-collidine (1.0 equiv.) in anhydrous CH$_2$Cl$_2$ was stirred at −45° C. A solution of perbenzoylated maltosylbromide (3.6 equiv.) mixed with CH$_2$Cl$_2$ was added dropwise to the resulting suspension. After stirring for 30 minutes at −45° C., the reaction mixture was heated to 0° C. and stirred for 30 minutes. After the completion of the reaction (indicated by TLC), pyridine was added to the reaction mixture, followed by dilution with CH$_2$Cl$_2$ and filtration over Celite. The resulting filtrate was washed sequentially with a 1M Na$_2$S$_2$O$_3$ aqueous solution, a 0.1M HCl aqueous solution and brine. An organic layer was dried with anhydrous Na$_2$SO$_4$, and the solvent was removed by a rotary evaporator. The residue as purified by silica gel column chromatography (EtOAc/hexane), obtaining VEG-2a as a glassy solid in 85% yield.

$^1$H NMR (400 MHz, CDCl$_3$): δ 8.10-7.80 (m, 18H), 7.60-7.10 (m, 42H), 5.66 (t, J=9.6 Hz, 3H), 5.56 (t, J=9.6 Hz, 3H), 5.41 (t, J=8.0 Hz, 3H), 4.42-4.39 (m, 3H), 4.16-4.14 (m, 3H), 3.88 (d, =8.0 Hz, 3H), 3.64 (d, =8.0 Hz, 3H), 3.36-3.46 (m, 4H), 3.38-3.25 (m, 4H), 3.22-3.15 (m, 4H), 2.55 (t, J=6.8 Hz, 2H), 2.15 (s, 3H), 2.11 (s, 3H), 2.06 (s, 3H), 1.88-1.72 (m, 2H), 1.54-1.50 (m, 3H), 1.43-1.05 (m, 21H), 0.87-0.83 (in, 12H); $^{13}$C NMR (100 MHz, CDCl$_3$): δ166.1, 165.8, 165.1, 164.8, 147.9, 147.7, 133.6, 133.4, 133.3, 133.1, 130.1, 129.8, 129.7, 129.6, 129.1, 129.0, 128.9, 128.5, 128.4, 128.3, 128.0, 127.9, 126.0, 122.8, 117.6, 101.4, 74.8, 72.7, 72.0, 71.6, 70.7, 69.7, 67.6, 63.0, 45.3, 40.4, 39.5, 37.7, 37.6, 37.5, 37.4, 37.3, 32.9, 32.8, 31.4, 28.0, 25.0, 24.5, 23.8, 23.7, 22.8, 22.7, 21.7, 20.7, 19.9, 19.7, 12.8, 12.0, 11.9.

<2-4> Synthesis of VEG-2 Through Deprotection

O-benzoylated VEG-2a was dissolved in MeOH and treated with a required amount of a methanol solution of 0.5M NaOMe, such that the final concentration of NaOMe was 0.05M. The reaction mixture was stirred for 6 hours at room temperature, and neutralized with Amberlit IR-120 (H±form). The resin was removed by filtration and washed with MeOH, and a solvent was removed from the combined filtrate in vacuo. 50 mL of diethyl ether was added to the residue dissolved in a 2 mL MeOH:CH$_2$Cl$_2$ (1:1) mixture, obtaining VEG-2 as a white solid in 921 % yield.

$^1$H NMR (400 MHz, CD$_3$OD): δ 4.35 (d, J=8.0 Hz, 3H). 4.02 (d, J=8.0 Hz, 3H), 3.83 (d, J=8.0 Hz, 4H), 3.75-3.74 (m, 4H), 3.68-3.62 (m, 8H), 3.37-3.17 (m, 15H), 2.55 (t, J=8.0 Hz, 2H), 2.15 (s, 3H), 2.11 (s, 3H), 2.02 (s, 3H), 1.76-1.71 (m, 2H), 1.53-1.36 (m, 8H), 1.28-1.18 (m, 12H), 1.1.4-1.07 (m, 7H), 0.86-0.83 (in, 12H); $^{13}$C NMR (100 MHz, CD$_3$OD): δ 149.2, 149.1, 128.8, 127.0, 123.8, 118.9, 105.1, 78.1, 77.8, 75.8, 75.2, 73.5 72.0, 71.7, 70.8, 69.9, 62.8, 46.7, 41.1, 41.0, 40.6, 38.8, 38.6, 38.5, 38.4, 34.0, 33.9, 32.7, 29.2, 26.0, 25.6, 24.2, 23.3, 23.2, 22.2, 21.7, 20.4, 20.3, 13.3, 12.4, 12.2; HRMS (FAB$^+$): calcd. for C$_{54}$H$_{94}$O$_{21}$ [M+Na]$^+$ 1101.6185, observed 1101.6189.

<Preparation Example 3> Synthesis of VEG-3

The synthetic scheme for VEG-3 is shown in FIG. 1. The VEG-3 compound was synthesized according to a synthetic method including Steps <3-1> to <3-3> below, and is shown in FIG. 2.

<3-1> Synthesis of Compound E of FIG. 1

A mixture of vitamin E (Compound A; DL-α-tocopherol, 16 mmol), methyl bromoacetate (22 mmol), anhydrous K$_2$CO$_3$ (35 mmol) and KI (8 mmol) in anhydrous acetone was stirred under an argon atmosphere to reflux overnight. After the removal of a solvent, the residue was dissolved in CH$_2$Cl$_2$, and extracted with water and brine. An organic layer was dried over anhydrous Na$_2$SO$_4$, filtered and concentrated under reduced pressure, thereby obtaining colorless oil. The oil was treated with serinol (25 mmol) dissolved in redistilled Me$^2$SO (20 mL) and anhydrous K$_2$CO$_3$ (35 mmol), and stirred for 6 hours at, 25° C. The reaction mixture was diluted with water, and extracted with Et$_2$O. An organic layer was washed with brine, and dried over anhydrous Na$_2$SO$_4$. After complete evaporation of a solvent, the residue was purified by fresh column chromatography (EtOAc/hexane), obtaining desired Compound E as a white solid in 85% yield.

$^1$H NMR (400 MHz, CDCl$_3$): δ 7.68 (d, =8.0 Hz, 1H), 4.20 (br s, 2H), 4.09-4.01 (m, 1H), 3.88-3.85 (m, 2H), 3.78-3.75 (m, 2H), 2.55 (t, 6.8 Hz, 2H), 2.15 (s, 3H), 2.11 (s, 3H), 2.06 (s, 3H), 1.88-1.72 (m, 2H), 1.54-1.50 (m, 3H), 1.43-1.05 (m, 21H), 0.87-0.83 (m, 12H); $^{13}$C NMR (100 MHz, CDCl$_3$): 170.3, 148.5, 146.8, 127.4, 125.5, 123.3, 117.8, 75.0, 71.1, 61.8, 52.3, 40.3, 40.2, 39.5, 37.7, 37.6, 37.6, 37.4, 32.9, 32.8, 31.2, 28.1, 24.9, 24.6, 23.8, 22.8, 22.7, 21.1, 20.7, 20.0, 19.8, 19.7, 19.6, 12.8, 12.0.

<3-2> Synthesis of VEG-3a Through General Procedure for Glycosylation

Under a N$_2$ atmosphere, a mixture of Compound E (1.0 equiv.), AgOTf (3.6 equiv.) and 2,4,6-collidine (1.0 equiv.) in anhydrous CH$_2$Cl$_2$ was stirred at −45° C. A solution of perbenzoylated maltosylbromide (2.4 equiv.) mixed with CH$_2$Cl$_2$ was added dropwise to the resulting suspension. After stirring for 30 minutes at −45° C., the reaction mixture was heated to 0° C. and stirred for 30 minutes. After the completion of the reaction (indicated by TLC), pyridine was added to the reaction mixture, followed by dilution with CH$_2$Cl$_2$ and filtration over Celite. The resulting filtrate/as washed sequentially with a 1M Na$_2$S$_2$O$_3$ aqueous solution, a 0.1M HCl aqueous solution and brine. An organic layer was dried with anhydrous Na$_2$SO$_4$, and the solvent was removed by a rotary evaporator. The residue was purified by silica gel column chromatography (EtOAc/hexane), obtaining VEG-3a as a glassy solid in 80% yield.

$^1$H NMR (400 MHz, CDCl$_3$): δ 8.09-7.93 (m, 14H), 7.89-7.86 (m, 4H), 7.82-7.80 (m, 4H), 7.76-7.71 (m, 4H), 7.64-7.58 (m, 2H), 7.53-7.16 (m, 42H), 6.18 (t, J=8.0 Hz, 2H), 5.73-5.64 (m, 4H), 5.40-5.33 (m, 2H), 5.21-5.13 (m, 4H), 4.72-4.56 (m, 4H), 4.39-4.10 (m, 10H), 3.85-3.80 (m, 2H), 3.39 (d, =8.0 Hz, 1H), 3.33 (t, J=8.0 Hz, 2H), 3.07 (d, J=8.0 Hz, 2H), 2.91 (t, J=8.0 Hz, 1H), 2.51 (t, J=6.8 Hz, 2H), 2.14 (s, 3H), 2.11 (s, 3H), 2.08 (s, 3H), 1.86-1.72 (m, 2H), 1.54-1.50 (m, 3H), 1.43-1.05 (m, 21H), 0.87-0.84 (m, 12H); $^{13}$C NMR (100 MHz, CDCl$_3$): δ 168.7, 166.2, 166.1, 166.0, 165.9, 165.8, 165.6, 165.5, 165.1, 165.0, 164.9, 164.8, 148.4, 147.1, 134.0, 133.7, 133.6, 133.5, 133.4, 130.1, 130.0, 129.9, 129.8, 129.7, 129.5, 129.3, 129.0, 128.9, 128.8, 128.7, 128.6, 128.5, 128.3, 127.5, 125.6, 123.2, 117.7, 100.9, 95.7, 74.9, 72.0, 71.4, 69.8, 69.1, 69.0, 62.6, 39.4, 37.6, 37.5, 37.4, 37.3, 32.8, 28.0, 24.9, 24.5, 24.0, 23.8, 22.8, 22.7, 21.1, 19.9, 19.8, 12.0, 11.9.

<3-3> Synthesis of VEG-3 Through Deprotection

O-benzoylated VEG-1a was dissolved in MeOH and treated with a required amount of a methanol solution of 0.5M NaOMe, such that the final concentration of NaOMe was 0.05M. The reaction mixture was stirred for 6 hours at room temperature, and neutralized with Amberlite IR-120 (H$^+$ form). The resin was removed by filtration and washed with MeOH, and a solvent was removed from the combined filtrate in vacuo. 50 mL of diethyl ether was added to the residue dissolved in a 2 mL MeOH:CH$_2$Cl$_2$ (1:1) mixture, obtaining VEG-3 as a white solid in 90% yield.

$^1$H NMR (400 MHz, CD$_3$OD): δ 5.13 (d, J=4.0 Hz, 2H), 4.42-4.39 (m, 1H), 4.36 (t, J=8.0 Hz, 2H), 4.14 (s, 2H), 4.04-3.98 (m, 2H), 3.91-3.86 (m, 3H), 3.81-3.74 (m, 6H), 3.68-3.57 (m, ION), 3.49 (t, J=8.0 Hz, 2H), 3.44-3.38 (m, 5H), 1.32-3.23 (m, 6H), 2.56 (t, J=8.0 Hz, 2H), 2.12 (s, 3H), 2.09 (s, 3H), 2.02 (s, 3H), 1.78-1.73 (m, 2H), 1.53-1.34 (m, 8H), 1.28-1.19 (m, 12H), 1.13-1.05 (m, 7H), 0.86-0.83 (in, 12H); $^{13}$C NMR (100 MHz, CD$_3$OD): δ 171.8, 149.6, 148.6, 128.5, 126.8, 124.1, 119.1, 104.8, 102.9, 81.3, 77.8, 76.7, 76.0, 75.1, 74.9, 74.8, 74.2, 72.3, 71.5, 69.4, 62.3, 50.6, 41.0, 40.6, 38.6, 38.5, 38.4, 34.0, 33.9, 33.8, 32.7, 29.2, 26.0, 25.5, 24.2, 23.3, 23.2, 22.2, 21.2, 20.8, 19.9, 19.8, 19.7, 19.6, 13.0, 12.2, 12.0; HRMS (FAB$^+$): calcd. for $C_{58}H_{99}NO_{25}$ [M=Na]$^+$ 1232.6404, observed 1232.6410.

<Preparation Example 4> Synthesis of VEG-4

The synthetic scheme for VEG-4 is shown in FIG. 1. The VEG-4 compound was synthesized according to a synthetic method including Steps <4-1> to <4-4> below, and is shown in FIG. 2.

<4-1> Synthesis of Compound C of FIG. 1

A mixture of vitamin E (Compound A; DL-α-tocopherol, 16 mmol), methyl bromoacetate (22 mmol), anhydrous $K_2CO_3$ (35 mmol) and KI (8 mmol) in anhydrous acetone was stirred under an argon atmosphere to reflux overnight. After the removal of a solvent, the residue was dissolved in $CH_2Cl_2$, and extracted with water and brine. An organic layer was dried over anhydrous $Na_2SO_4$, filtered, and concentrated under reduced pressure. After complete removal of a solvent, $LiAlH_4$ (14.0 mmol) was slowly added to the residue dissolved in THF at 0° C. The mixture was stirred for 4 hours at room temperature, and the reaction was quenched by sequentially adding MeOH, water and a 1.0N HCl aqueous solution at 0° C., followed by extraction with $CH_2Cl_2$ twice. Combined organic layers were washed with brine, and dried over anhydrous $Na_2SO_4$. The residue was purified by silica gel column chromatography (EtOAc/hexane), obtaining desired Compound C in 85% yield.

$^1$H NMR (400 MHz, $CDCl_3$): δ 3.92-3.90 (m, 2H), 3.77-3.75 (m, 2H), 2.75 (br s, 1H), 2.57 (t, J=6.8 Hz, 2H), 2.17 (s, 3H), 2.13 (s, 3H), 2.08 (s, 3H), 1.88-1.72 (m, 2H), 1.54-1.50 (m, 3H), 1.43-1.05 (m, 21H), 0.88-0.84 (m, 12H); $^{13}$C NMR (100 MHz, $CDCl_3$): δ 148.1, 147.7, 127.8, 125.8, 123.0, 117.0, 74.9, 73.9, 62.4, 53.5, 40.3, 40.2, 39.5, 37.8, 37.7, 37.6, 37.5, 37.4, 33.0, 32.9, 32.8, 31.4, 31.3, 28.1, 25.0, 24.9, 24.6, 24.0, 22.9, 22.8, 21.2, 20.8, 19.9, 19.6, 12.8, 11.9.

<4-2> Synthesis of Compound F of FIG. 1

A mixture of Compound C (1.0 equiv.), $PPh_3$ (1.5 equiv.) and $CBr_4$ (1.2 equiv.) in anhydrous $CH_2Cl_2$ was stirred at room temperature for 4 hours under argon. The resulting solution was washed with $NaHCO_3$ and brine, dried over $Na_2SO_4$ and then filtered. A product was obtained by evaporating the filtrate, and used in the subsequent step without additional purification. The product was added to a solution prepared by stirring diethyl malonate (1.0 equiv.) and NaH (1.0 equiv.) in ethanol. The resulting mixture was heated under reflux for 4 hours. After cooling to room temperature, water was added, the product was extracted with $Et_2O$, dried over $Na_2SO_4$, and a solvent was removed using a rotary evaporator to obtain a product. The resulting product was further treated with $LiAlH_4$ (3.5 equiv.) mixed with dry THF for 4 hours at room temperature. After the reaction was quenched, water was added dropwise to the resulting solution, and extracted with $CH_2Cl_2$ twice. The combined extracts were washed with 1.0M HCl and brine, dried over $Na_2SO_4$, and concentrated in vacuo. The residue was purified by silica gel column chromatography (EtOAc/hexane), obtaining desired Compound F in 80% yield.

$^1$H NMR (400 MHz, $CDCl_3$): δ 3.83-3.78 (m, 2H), 3.75-3.70 (m, 4H), 3.05 (br s, 2H), 2.56 (t, J=6.8 Hz, 2H), 2.15 (s, 3H), 2.11 (s, 3H), 2.06 (s, 3H), 1.88-1.76 (m, 2H), 1.74-1.70 (m, 2H), 1.69-1.67 (m, 1H), 1.54-1.50 (m, 3H), 1.43-1.05 (m, 21H), 0.87-0.83 (m, 12H); $^{13}$C NMR (100 MHz, $CDCl_3$): δ 148.2, 148.1, 127.8, 125.9, 123.4, 117.7, 75.0, 71.3, 65.7, 40.5, 40.3, 40.2, 39.5, 37.7, 37.6, 37.5, 37.4, 33.0, 32.9, 32.8, 31.4, 31.3, 29.1, 28.1, 25.0, 24.6, 24.0, 22.9, 22.8, 21.2, 20.8, 19.9, 19.8, 19.7, 19.6, 13.0, 12.2, 12.0.

<4-3> Synthesis of VEG-4a Through General Procedure for Glycosylation

Under a $N_2$ atmosphere, a mixture of Compound F (1.0 equiv.), AgOTf (3.6 equiv.) and 2,4,6-collidine (1.0 equiv.) in anhydrous $CH_2Cl_2$ was stirred at −45° C. A solution of perbenzoylated maltosylbromide (2.4 equiv.) mixed with $CH_2Cl_2$ was added dropwise to the resulting suspension. After stirring for 30 minutes at −45° C., the reaction mixture was heated to 0° C. and stirred for 30 minutes. After the completion of the reaction (indicated by TLC), pyridine was added to the reaction mixture, followed by dilution with $CH_2Cl_2$ and filtration over Celite. The resulting filtrate was washed sequentially with a 1M $Na_2S_2O_3$ aqueous solution, a 0.1M HCl aqueous solution and brine. An organic layer was dried with anhydrous $Na_2SO_4$, and the solvent was removed by a rotary evaporator. The residue was purified by silica gel column chromatography (EtOAc/hexane), obtaining VEG-4a as a glassy solid in 78% yield.

$^1$H NMR (400 MHz, $CDCl_3$): δ 8.11 (d, J=8.0 Hz, 2H), 8.05-7.93 (m, 12H), 7.87-7.85 (m, 6H), 7.81-7.78 (m, 2H), 7.74-7.72 (m, 6H), 7.53-7.18 (m, 42H), 6.15 (t, J=8.0 Hz, 2H), 5.81 (t, J=4.0 Hz, 2H), 5.71-5.62 (m, 4H), 5.37-5.24 (m, 4H), 5.19-5.09 (m, 2H), 4.77-4.08 (n, 12H), 3.74-3.72 (in, 2H). 3.60-3.44 (m, 4H), 3.30-3.27 (m, 2H), 3.16 (d, J=4.0 Hz, 1H), 3.05 (d, J=8.0 Hz, 1H), 2.99 (d, J=8.0 Hz, 1H), 2.85 (d, J=8.0 Hz, 1H), 2.53 (t, J=6.8 Hz, 2H), 2.15 (s, 3H), 2.11 (s, 3H), 2.06 (s, 3H), 1.88-1.76 (m, 2H), 1.74-1.70 (m, 2H), 1.69-1.67 (m, 1.1-1), 1.54-1.50 (m, 3H), 1.43-1.05 (in, 21H), 0.88-0.84 (m, 12H); $^{13}$C NMR (100 MHz, $CDCl_3$): δ 166.2, 166.1, 165.9, 165.8, 165.5, 165.2, 165.1, 164.0, 164.9, 148.3, 147.6, 133.7, 133.6, 133.5, 133.4, 133.3, 133.2, 130.1, 130.0, 129.9, 129.8, 129.7, 129.6, 129.5, 129.4, 129.3, 129.0, 128.9, 128.8, 128.7, 128.6, 128.5, 128.4, 128.3, 127.8, 125.8, 122.7, 117.5, 74.7, 72.3, 72.1, 71.3, 70.2, 69.8, 69.1, 69.0, 39.4, 37.5, 37.4, 37.3, 32.8, 32.7, 28.0, 25.0, 24.5, 23.9, 22.8, 22.7, 21.1, 20.6, 20.0, 19.8, 12.8, 12.0, 11.8.

<4-4> Synthesis of VEG-4 Through Deprotection

O-benzoylated VEG-4a was dissolved in MeOH and treated with a required amount of a methanol solution of 0.5M NaOMe, such that the final concentration of NaOMe was 0.05M. The reaction e was stirred for 6 hours at room temperature, and neutralized with Amberlite IR-120 (H$^+$ form). The resin was removed by filtration and washed with MeOH, and a solvent was removed from the combined filtrate in vacuo. 50 mL of diethyl ether was added to the residue dissolved in a 2 mL MeOH:$CH_2Cl_2$. (1:1) mixture, obtaining VEG-4 as a white solid in 90% yield.

$^1$H NMR (400 MHz, $CD_3OD$): 5.16 (d, J=4.0 Hz, 2H), 4.35 (d, J=8.0 Hz, 2H), 4.02-3.96 (d, J=4.0 Hz, 2H), (m, 2H), 3.90-3.58 (m, 22H), 3.52 (t, J=8.0 Hz, 2H), 3.45-3.42 (m, 2H), 3.39-3.33 (m, 4H), 3.30-3.23 (m, 6H), 2.56 (t, J=8.0 Hz, 2H), 2.26-2.22 (m, 1H), 2.13 (s, 3H), 2.09 (s, 3H), 2.02 (s, 3H), 1.91-1.85 (m, 2H), 1.78-1.73 (m, 2H), 1.58-1.35 (m, 8H), 1.29-1.19 (m, 12H), 1.16-1.05 (m, 7H), 0.87-0.84 (m, 12H); $^{13}$C NMR (100 MHz, $CD_3OD$): J 149.6, 149.0, 128.7, 126.9, 123.8, 118.8, 104.9, 104.7, 103.0, 81.4, 77.9, 76.6, 75.8, 74.8, 74.2, 72.2, 71.6, 71.3, 70.8, 62.8, 62.3, 40.9, 40.6, 38.6, 38.5, 38.4, 38.1, 38.0, 34.0, 339, 32.8, 30.2, 29.2, 26.0, 25.5, 24.3, 23.3, 23.2, 22.1, 21.7, 20.4, 20.3, 13.3, 1.2.4, 12.2; HRMS (FAB$^+$): calcd. for $C_{58}H_{100}O_{24}$ [M+Na]$^+$ 1203.6502, observed 1203.6504.

<Preparation Example 5> Synthesis of VEG-5

The synthetic scheme for VEG-5 is shown in FIG. 1. The VEG-5 compound was synthesized according to a synthetic method including Steps <5-1> to <5-3> below, and is shown in FIG. 2.

<5-1> Synthesis of Compound G Through Glycosylation and Deprotection

Under a $N_2$ atmosphere, a mixture of vitamin E (Compound A; DL-α-tocopherol, 1.0 equiv.), AgOTf (3.6 equiv.) and 2,4,6-collidine (1.0 equiv.) in anhydrous $CH_2Cl_2$ was stirred at −45° C. A solution of perbenzoylated maltosylbromide (1.2 equiv.) mixed with $CH_2Cl_2$ was added dropwise to the resulting suspension. After stirring for 30 minutes at −45° C., the reaction mixture was heated to 0° C. and stirred for 30 minutes. After the completion of the reaction (indicated by TLC), pyridine was added to the reaction mixture, followed by dilution with $CH_2Cl_2$ and filtration over Celite. The resulting filtrate was washed sequentially with a 1M $Na_2S_2O_3$ aqueous solution, a 0.1M HCl aqueous solution and brine. An organic layer was dried with anhydrous $Na_7SO_4$, and the solvent was removed by a rotary evaporator. The O-benzoylated product was dissolved in MeOH, and treated with a required amount of a methanol solution of 0.5M NaOMe, such that the final concentration of NaOMe was 0.05M. The reaction mixture was stirred for 6 hours at room temperature, and neutralized with Amberlite IR-120 ($H^+$ form) resin. The resin was removed by filtration and washed with MeOH, and a solvent was removed from the combined filtrate in vacuo. 50 mL of diethyl ether was added to the residue dissolved in a 2 mL MeOH:$CH_2Cl_2$ (1:1) mixture, obtaining Compound G as a white solid in 88% yield.

$^1$H NMR (400 MHz, $CD_3OD$): δ 4.52 (d, J=8.0 Hz, 1H), 3.77-3.74 (m, 1H), 3.65-3.62 (m, 1H), 3.52-3.48 (m, 1H), 3.44-3.40) (m, 1H), 3.31 (s, 2H), 2.58 (t, =6.8 Hz, 2H), 2.22 (s, 3H), 2.18 (s, 3H), 2.04 (s, 3H), 1.88-1.76 (m, 2H), 1.74-1.70 (m, 2H), 1.69-1.67 (m, 1H), 1.54-1.50 (m, 3H), 1.43-1.05 (m, 21H), 0.87-0.83 (m, 12H); $^{13}$C NMR (100 MHz, $CD_3OD$): δ 149.4, 147.4, 129.9, 129.8, 128.0, 123.5, 118.6, 106.2, 78.1, 77.9, 75.9, 75.8, 71.9, 63.0, 40.6, 38.6, 38.5, 34.1, 34.0, 33.9, 29.3, 26.0 25.6, 24.3, 23.3, 23.2, 21.8, 20.4, 20.3, 14.3, 13.4, 12.1, 12.0.

<5-2> Synthesis of VEG-5a Through General Procedure for Glycosylation

Under a $N_2$ atmosphere, a mixture of Compound G (1.0 equiv.), AgOTf (3.6 equiv.) and 2,4,6-collidine (1.0 equiv.) in anhydrous $CH_2Cl_2$ was stirred at −45° C. A solution of perbenzoylated maltosylbromide (5.0 equiv.) mixed with $CH_2Cl_2$ was added dropwise to the resulting suspension. After stirring for 30 minutes at −45° C., the reaction mixture was heated to 0° C. and stirred for 30 minutes. After the completion of the reaction (indicated by TLC), pyridine was added to the reaction mixture, followed by dilution with $CH_2Cl_2$ and filtration over Celite. The resulting filtrate was washed sequentially with a 1M $Na_2S_2O_3$ aqueous solution, a 0.1M HCl aqueous solution and brine. An organic layer was dried with anhydrous $Na_2SO_4$, and the solvent was removed by a rotary evaporator. The residue was purified by silica gel column chromatography (EtOAc/hexane), obtaining VEG-5a as a glassy solid in 70% yield.

$^1$H NMR (400 MHz, $CDCl_3$): δ 8.26 (d, J=8.0 Hz, 2H), 8.15-7.80 (m, 24H), 7.72-6.67 (m, 5H), 7.66-7.59 (m, 3H), 7.58-7.12 (m, 46H), 5.90-5.75 (m, 4H), 5.71-4.45 (m, 7H), 5.34 (t, J=8.0 Hz, 1H), 4.95 (d, J=8.0 Hz, 1H), 4.82-4.75 (m, 4H). 4.62-4.56 (m, 3H), 4.47-4.35 (in 4H), 4.16-4.08 (m, 2H), 4.04-4.01 (m, 1H), 3.92-3.85 (m, 3H), 3.80-3.68 (m, 2H), 3.02 (brs, 1H), 2.56 (t, J=6.8 Hz, 2H), 2.17 (s, 3H), 2.16 (s, 3H), 2.02 (s, 3H), 1.88-1.75 (m, 2H), 1.74-1.70 (m, 2H) 1.69-1.67 (m, 1H), 1.54-1.50 (m, 3H), 1.43-1.05 (m, 21H), 0.87-0.84 (m, 12H); $^{13}$C NMR (100 MHz, $CDCl_3$): 166.2, 165.9, 165.3, 165.2, 165.1, 133.7, 133.5, 133.2, 130.2, 129.9, 129.8, 129.7, 129.6, 129.5, 129.3, 129.0, 128.8, 128.6, 128.5, 128.4, 128.0, 122.4, 74.8, 74.6, 74.2, 72.5, 72.4, 72.3, 72.1, 69.8, 69.1, 39.5, 37.6, 37.5, 32.9, 28.1, 25.0, 24.6, 22.9, 22.8, 19.9, 19.8, 14.2, 13.3, 12.1, 11.9.

<5-3> Synthesis of VEG-5 Through Deprotection

O-benzoylated VEG-5a was dissolved in MeOH and treated with a required amount of a methanol solution of 0.5M NaOMe, such that the final concentration of NaOMe was 0.05M. The reaction mixture was stirred for 6 hours at room temperature, and neutralized with Amberlite IR-120 ($H^+$ form). The resin was removed by filtration and washed with MeOH, and a solvent was removed from the combined filtrate in vacuo. 50 mL of diethyl ether was added to the residue dissolved in a 2 mL MeOH:$CH_2Cl_2$ (1:1) mixture, obtaining VEG-5 as a white solid in 88% yield.

$^1$H NMR (400 MHz, $CD_3OD$): δ 4.99 (d, J=8.0 Hz, 1H), 4.93 (d, J=8.0 Hz. 1H), 4.72 (d, J=8.0 Hz, 1H), 4.65 (d, J=8.0 Hz, 1H), 4.26 (d, =8.0 Hz, 1H), 4.20-4.09 (m, 4H), 3.87-3.75 (m, 5H), 3.69-3.55 (m, 5H), 3.41-3.12 (m, 0.2H), 2.57 (t, J=8.0 Hz, 2H), 2.20 (s, 3H), 2.17 (s, 3H), 2.01 (s, 3H), 1.78-1.73 (m, 2H), 1.52-1.36 (m, 8H), 1.28-1.18 (m, 12H), 1.12-1.07 (m, 7H), 0.85-0.82 (m, 12H); $^{13}$C NMR (100 MHz, $CD_3OD$): δ 149.6, 147.5, 123.7, 123.6, 118.8, 104.8, 104.5, 103.8, 103.0, 102.4, 81.4, 79.9, 78.1, 78.0, 77.9, 77.8, 75.9, 75.3, 75.2, 71.9, 71.8, 71.6, 71.5, 69.6, 62.9, 62.7, 41.1, 40.6, 38.8, 38.6, 38.5, 38.4, 34.0, 33.9, 29.2 26.0, 25.5, 24.2, 23.3, 23.2, 22.2, 21.8, 20.4, 20.3, 20.2, 14.6, 14.5, 13.7, 12.1, 12.0; HRMS ($FAB^+$): calcd. for $C_{59}H_{100}O_{27}$ $[M+Na]^+$ 1263.6350 observed 1263.6353.

<Example 1> Properties of VEGs

To identify the properties of VEGs synthesized according to the synthetic methods of Preparation Examples 1 to e molecular weights (M.W.) and critical micellar concentrations (CMCs) of VEGs, and the hydrodynamic radii ($R_h$) of formed micelles were measured.

Specifically, the CMCs were measured using hydrophobic fluorescence staining and diphenylhexatriene (DPH), and the hydrodynamic radii ($R_h$) of the micelles formed by each formulation were measured by dynamic light scattering (DLS). The results were compared with that of a conventional amphiphilic molecule (detergent), that is, DDM, and are shown in Table 1.

TABLE 1

| Detergent | MW[a] | CMC (mM) | CMC (wt %) | $R_h$ (nm)[b] |
|---|---|---|---|---|
| VEG-1 | 1035.3 | ~0.002 | ~0.0002 | 4.2 ± 0.1 |
| VEG-2 | 1079.3 | ~0.003 | ~0.0003 | 4.7 ± 0.1 |
| VEG-3 | 1210.4 | ~0.002 | ~0.0002 | 4.8 ± 0.1 |
| VEG-4 | 1181.4 | ~0.003 | ~0.0003 | 5.1 ± 0.1 |
| VEG-5 | 1241.4 | ~0.002 | ~0.0002 | 3.9 ± 0.1 |
| DDM | 510.1 | 0.170 | 0.0087 | 3.4 ± 0.0 |

[a]Molecular weight of detergents.
[b]Hydrodynamic radius of micelles was determined at 1.0 wt % by dynamic light scattering.

The CMC values of VEGs were much smaller than that of DDM. Therefore, since VEGs easily formed micelles at a low concentration, it can be seen that hey tended to highly agglomerate in an aqueous solution, compared to DDM.

In addition, although having different hydrophilic structures, VEGs had similar CMC values. It is determined that this is because the micelle formation of an amphipathic molecule is mainly induced by a hydrophobic effect, and all VEGs commonly contain vitamin E as a hydrophobic group.

The distribution of sizes of the micelles formed by VEGs was shown in a narrow range of 3.8 to 5.2 nm, indicating that a larger micelle is formed, compared to DDM. As an additional result of analyzing the size distribution of the micelles formed by VEGs, it was confirmed that most VEGs form micelles with a uniform, size (FIGS. 4 and 5).

<Example 2> Evaluation of Ability of VEGs to Stabilize R. capsulatus Superassembly (LHI-RC) Structure (FIG. 5)

An experiment was conducted to evaluate the ability of VEGs to stabilize the structure of LHI-RC. The photosynthetic superassembly consists of a complex of light-Harvesting complex I (LHI) and a reaction center (RC). The structural stability of LHI-RC was measured by a method of monitoring the structure of a protein for 20 days using UV-Vis spectroscopy. As amphipathic molecules, all VEGs of the present invention and conventional amphipathic molecules DDM and OG were used, and the concentrations of the amphipathic molecules were measured at CMC+0.04 wt % (FIG. 5A) and CMC+0.2 wt % (FIG. 59), and the stability of the LHI-RC protein was investigated according to the concentration of an amphipathic molecule.

Specifically, LHI-RC stability was measured using a method disclosed in the paper published in 2008 by the inventors (P. S. Chae et al., ChemBioChem 2008, 9, 1706-1709). Briefly, the inventors used the membrane obtained from *R. capsulatus*, U43 [pUHTM86Bgl] which does not have light-harvesting complex II (LHII). A 10 mL aliquot of the solution of the frozen *R. capsulatus* membrane was homogenized using a glass homogenizer, and incubated with gentle stirring at 32° C. for 30 minutes. The homogenized membrane was treated with 1.0 wt % DDM for 30 minutes at 32° C. Membrane debris was subjected to ultracentrifugation, thereby collecting a pellet. 200 μL of $Ni^{2+}$-NTA resin (pre-equilibrated and stored in a buffer containing 10 mM Tris, pH 7.8) was added to a supernatant containing the LHI-RC complex solubilized in DDM, and incubated at 4° C. for 1 hour. The resin-containing solution was filtrated using 1.0 HisSpinTrap columns, and each column was washed twice with a 500 μL binding buffer containing 10 mM Tris (pH 7.8), 100 mL NaCl and 1×CMC DDM. Following the replacement with a new ultracentrifuge tube, the LHI-RC complex purified by DDM was eluted using a buffer containing 1M imidazole (2×300 μL). 80 μL of the protein sample was diluted with 920 μL of each of VEGs, DDM and OG so that the final concentration was CMC+0.04 wt % or CMC+0.2 t %. The LHI-RC complex produced in each detergent was incubated for 20 days at 25° C., and then the incubation temperature increased to 32° C. for 7 days. Protein stability was measured at regular intervals during the cubation by measuring UV-Vis spectra of the samples in the range of 650 to 950 nm. Protein integrity was evaluated by monitoring absorbance (A875) at 875 nm.

All VEGs were superior to DDM in terms of the ability to maintain the integrity of the LHI-RC complex, and particularly, VEG-3 showed the most excellent effect (FIG. 6). When the concentration of an amphipathic compound increased to CMC+0.2 wt %, the difference in efficacy between DDM and VEGs increased. In addition, like DDM, when the incubation temperature increased to 32° C., the amphipathic compounds according to the present invention was reduced in ability to stabilize the complex, but the protein degradation in VEGs occurred significantly slower, compared to DDM, indicating that VEGs have an excellent ability to stabilize a membrane protein complex (FIG. 6).

<Example 3> Evaluation of Ability of VEGs to Stabilize Structure of UapA Membrane Protein $UapAG411V_{A1-11}$ (hereinafter, referred to as "UapA") was expressed in a *Saccharomyces cerevisiae* FGY217 strain by GFP fusion, and isolated into a sample buffer (20 mM Tris (pH 7.5), 150 mM NaCl, 0.03% DDM, 1 mM xanthine), which was performed according to the method disclosed in the paper written by J. Leung et al. (*Mol. Menthr. Biol.* 2013, 30, 32-42). The protein was concentrated to be approximately 10 mg/ml using a 100 kDa molecular weight cutoff filter (Millipore). The protein was diluted 1:150 with a buffer containing DDM, VEG (VEG-1, VEG-2, VEG-3, VEG-4 or VEG-5) or LMNG at CMC+0.2 wt % in Greiner 96. CPM dye (Invitrogen) stored in DMSO (Sigma) was diluted with a dye buffer (20 mM Tris (pH 7.5), 150 mM NaCl, 0.03% DDM, 5 mM EDTA), and 3 μL of the diluted dye was added to an individual protein sample. The reaction mixture was treated at a constant temperature of 40° C. for 120 minutes. A fluorescence emission intensity was monitored using a microplate spectrofluorometer set to excitation and emission wavelengths of 387 and 463 nm, respectively. The maximum fluorescence value was used to calculate the percentage of a protein folded during incubation. The relative amount of the folded protein was plotted over time using GraphPad Prism.

The membrane containing UapA was resuspended in a pH 8.0 PBS buffer containing 10 mM imidazole, 150 mM NaCl and 10% glycerol, and a protein concentration was measured. The membrane was adjusted to a concentration of 1 mg/ml, and a 1 ml aliquot was incubated for 60 minutes with each of 1.0 mL of DDM, LMNG, VEG-3 and VEG-5, on ice under stirring. A 100 uL aliquot was obtained from each tube and subjected to ultracentrifugation for 10 minutes at 150, 000 g, and then fluorescent SEC (FSEC) was performed on each sample. The remaining soluble fractions were incubated for 10 minutes at 45° C. The thermally-treated samples were applied to FSEC to monitor the integrity of a transporter. FSEC was performed using a Superose6 column (GE Healthcare) equilibrated with a buffer containing an appropriate preparation (DDM, LMNG, VEG-3 or VEG-5).

As shown in FIG. 7, VEG-3 and VEG-5 have an excellent ability to maintain UapA in a structurally stable state in an aqueous solution, compared to LMNG and DDM. Other VEGs (VEG-1, 2 and 4) showed similar results to DDM under the tested conditions.

As a result of performing additional FSEC comparison experiments with LMNG and DDM with respect to VEG-3 and VEG-5 having excellent effects, LMNG and DDM were superior to VEG-3 and VEG-5 in terms of the ability to extract and solubilizing a membrane protein. However, when thermally treated at 45° C., UapA solubilized by LMNG and DDM was considerably degraded, but UapA solubilized by VEG-3 and VEG-5 maintained protein integrity (FIG. 8). Therefore, it can be seen that VEG-3 and VEG-5 exhibited excellent effects of maintaining UapA extracted from a cell membrane in a structurally stable state in an aqueous solution, and thus they are able to be effectively used to stabilize a membrane protein.

<Example 4> Evaluation of Ability of VEGs to Stabilize MelB Membrane Protein Structure An experiment was conducted to measure the structural stability of a *Salmonella typhimurium* melibiose per urease (MelB) protein by VEGs.

Specifically, *Salmonella typhimurium* MelB$_{St}$ (melibiose permease) having a 10 His tag at the C-terminus was expressed in *E. coli* DW2 cells (ΔmelB and ΔlacZY) using a pK95ΔAHB/WT MelB$_{St}$/CH10 plasmid. Cell growth and membrane preparation were carried out according to the methods disclosed in the paper written by A. S. Ethayathulla et al. (*Nat. Commun.* 2014, 5, 3009). A protein assay was performed using a Micro BCA kit (Thermo Scientific, Rockford, Ill.). MelB$_{St}$ stability in VEGs or DDM was evaluated using the protocol disclosed in *Nat. Methods* 2010, 7, 1003-1008, written by P. S. Chae et al. A MelB$_{St}$-containing membrane sample (the final protein concentration was 10 mg/mL) was incubated in a solubilization buffer containing 1.5% (w/v) DDM or VEGs (50 mM sodium phosphate, pH 7.5, 200 mM NaCl, 10% glycerol, 20 mM melibiose) at two different temperatures (0 and 23° C.) for 90 minutes. To remove an insoluble material, ultracentrifugation was performed using a Beckman Optima™ MAX ultracentrifuge equipped with a TLA-100 rotor at 355,590 g and 4° C. for 30 minutes. 20 μg of the membrane protein which did not undergo ultracentrifugation was applied to an untreated membrane or the same amount of extracts of the compounds after ultracentrifugation, and the treated samples were loaded in respective wells at an equal volume. The loaded samples were analyzed by SDS-15% PAGE, and then visualized by immunoblotting with a Penta-His-HRP antibody (Qiagen, Germantown, Md.).

To assess the thermal stability of MelB$_{St}$ in various amphipathic molecules, MelB$_{St}$ extracted with individual amphipathic molecules at 23° C. was subjected to additional thermal treatment at three different temperature (45, 55 and 65° C.) and ultracentrifugation, followed by SDS-15% PAGE and Western blotting. MelB$_{St}$ was detected using a SuperSignalWest Pico chemiluminescent substrate by an ImageQuant LAS 4000 Biomolecular Imager (GE Healthcare Life Science).

As the result shown in FIGS. 9A to 9D, at 0° C. and 23° C., DDM is more efficient in extracting/solubilizing MelB$_{St}$ from a cell membrane, compared to VEGs.

However, when the temperature increased to 45° C., DDM and VEGs solubilized the MelB$_{St}$ protein with almost similar efficiencies, and at a higher temperature (55° C.), the MelB$_{St}$ solubilization efficiency of DDM showed a significant decrease, whereas most VEGs did not show a significant decrease in MelB$_{St}$ solubilization efficiency at 55° C. Particularly, the efficiency of VEG-4 and VEG-5 remained intact. At 65° C., all VEGs showed excellent MelB$_{St}$ solubilization ability, compared to DDM, and particularly, VEG-3 and VEG-4 showed very excellent protein solubilization ability even at a high temperature.

Overall, at low temperatures (0° C. and 23° C.), DDM showed higher protein extraction efficiency than VEGs, but in a protein thermal stability experiment performed at elevated temperatures, VEGs (particularly, VEG-3 and VEG-4) showed, a higher transporter solubilization ability than DDM, indicating excellent protein stabilization ability.

<Example 5> Evaluation of Ability of VEGs to Stabilize β$_2$AR Protein

<5-1> Measurement of Long-Term Stability

A receptor was expressed in Sf9 insect cells infected with Baculovirus and solubilized in 1% DDM. The DDM-solubilized receptor was purified by alprenolol-sepharose in the presence of 0.01% cholesteryl succinate (CHS). β$_2$AR purified by DDM was diluted with a buffer containing DDM or VEGs (VEG-1, VEG-2, VEG-3 and VEG-5) to reach the final concentration of CMC+0.2 wt %. β$_2$AR solubilized in each compound was stored for 10 days at room temperature, and the ligand binding ability of the receptor was measured at regular intervals by incubating the receptor with 10 nM radioactive [$^3$H]-dihydroalprenolol (DHA) for 30 minutes at room temperature. The mixture was loaded into a G-50 column, and a supernatant was collected using a certain amount of binding buffer (supplemented with 20 nM HEPES pH 7.5, 100 mM NaCl, 0.5 mg/ml BSA). In addition, a 15 ml scintillation fluid was added. Receptor-binding [$^3$H]-DHA was measured using a scintillation counter (Beckman).

As a result, VEGs (VEG-1, VEG-2, VEG-3 and VEG-5) showed the ability to maintain initial activity of the solubilized receptor, which was similar to DDM (FIG. 11). However, in terms of long-term receptor stabilization ability, the receptors solubilized by DDM and VEG-5 showed rapid loss of activity over time, and receptors solubilized in VEG-2 and VEG-3 showed that the activity of the receptors was consistently maintained during incubation for 10 days (FIG. 10A). Therefore, VEG-2 and VEG-3 are determined to be effective in research on a solubilized receptor protein than DDM.

<5-2> Purification and Measurement of Stability of β$_2$AR-G$_s$ Complex Solubilized in VEG-3

100 μM β$_2$AR solubilized in 0.1% DDM mixed with 120 μM G$_s$ heterotrimer for 30 minutes at room temperature. 0.5-unit apyrase (NEB) and 2 mM MgCl$_2$ were added to facilitate complex formation, followed by further incubation for one hour. Subsequently, 1.0% VEG-3 was added such that the final concentration reached 0.2%, and the sample was further incubated for 30 minutes to change DDM to VEG-3. The protein solution was loaded into a M1 Flag column, washed with a series of buffers with different molar ratios of 0.1% DDM buffer to 0.5% VEG-3 buffer to completely change DDM to VEG-3, and the receptor-G$_s$ complex was finally eluted with a 0.05% VEG-3 buffer. Preparative gel filtration was performed to purify the β$_2$AR-G$_s$ complex with a running buffer (20 mM HEPES pH 7.5, 100 mM NaCl, 0.005% DTM-A6, 1 mM BI, 100 mM TCEP). To measure the stability of the β$_2$AR-G$_s$ complex in VEG-3, analytical gel filtrations were performed using the running buffer as above, but after 3 and 15-day incubation, performed without VEG-3 (compound-free condition).

As the result shown in FIG. 10B, it was confirmed that, in contrast to the result obtained from the β$_2$AR-G$_s$ complex purified by DDM in the previous study, the β$_2$AR-G$_s$ complex purified by VEG-3 continuously maintains its integrity as a complex for 15 days. In the case of DDM, the complex showed significant dissociation between the receptor and G$_s$ protein even after 2 day-incubation.

<5-3> Negative Stain EM Analysis of NAR-G$_s$ Complex Solubilized in VEG-3

A β$_2$AR-G$_s$ protein complex was prepared for electron microscopy using a conventional negative staining protocol, and imaged at room temperature using a Tecnai T12 electron microscope operated at 120 kV according to a low-dose procedure. Images recorded at a magnification of 71,138× and a defocus value of approximately −1.1 urn on a Gatan US4000 CCD camera. All images were binned (2×2 pixels) to obtain a pixel size of 4.16 Å at a specimen level. Particles were manually removed using e2boxer (part of the EMAN2 software suite). 2D reference-free alignment and classification of particle projections were performed using ISAC. 23,035 projections of β$_2$AR-G$_s$ were subjected to ISAC producing 19 classes consistent in two-way matching and 5401 particle projections.

As a result, it was seen that particles generated from the β$_2$AR-G$_s$ complex purified by VEG-3 are highly homogeneous, different from the aggregation of particles observed in the DDM-purified complex in the previous study. In addition, in representative 2D class images, individual components (β$_2$AR, G$_{\alpha s}$ and G$_{\beta\gamma}$) of the complex were clearly distinguished (FIGS. 12B and 12C). The EM images of the protein complex obtained by the use of VEG-3 was clearer and more distinct than the images of complexes obtained using other amphiphilic molecules. This show that the amphiphilic compounds of the present invention have a significant potential to explain the structure and dynamic structural change of a membrane protein complex through EM analysis.

<Example 6> Evaluation of Ability of VEGs to Stabilize Membrane Protein (LeuT) Structure Wild-type LeuT derived from *Aquifex aeolicus* was purified according to the method disclosed in the paper written by G. Deckert et al. (*Nature* 1998, 392, 353-358). LeuT is expressed in *E. coli* C41 (DE3) transformed with pET16b encoding a C-terminal 8xHis-tagged transporter (the expression plasmid was provided by Dr E. Gouaux, Vollum Institute, Portland, Oreg., USA). Briefly, a LeuT protein was isolated and solubilized in 1.0 wt % DDM, and then the protein was bound to Ni$^{2+}$-NTA resin (Life Technologies, Denmark), followed by elution with 20 mM Tris-HCl (pH 8.0), 1 mM NaCl, 199 mM KCl, 0.05% DDM and 300 mM imidazole. Afterward, approximately 1.5 mg/nal of a protein sample (stock) was diluted 10-fold with an identical buffer which does not include DDM or imidazole, but is supplemented with each of VEGs or DDM (control) to obtain a final concentration of CMC+0.04 wt %. The protein sample was stored for 10 days at room temperature, and then centrifuged at regular intervals during the incubation prior to the measurement of protein activity. Protein activity was determined by measuring [$^3$H]-Leu binding using SPA (M. Quick et al., *Proc. Natl, Acad. Sci. U.S.A.* 2007, 104, 3603-3608). The assay was performed on samples containing 450 mM NaCl and each compound at the final concentration. In the presence of 20 nM [$^3$H]-Leu and 1.25 mg/mL of copper chelate (His-Tag) YSi beads (both purchased from PerkinElmer, Denmark), a SPA reaction was perform. [$^3$H]-Leu binding was measured using a MicroBeta liquid scintillation counter (PerkinElmer).

As the result shown in FIG. 13, VEG-5 among VEGs showed an ability to maintain LeuT transporter activity similar to DDM.

The invention claimed is:

1. A compound represented by Formula 1 or 2 below:

[Formula 1]

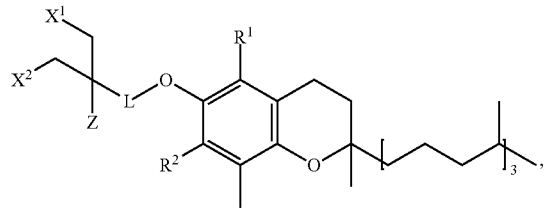

where R$^1$ and R$^2$ are each independently hydrogen (H) or CH$_3$; L is —CH$_2$—, —CH$_2$CH$_2$—, —NHCOCH$_2$—, —CH$_2$OCH$_2$CH$_2$— or a direct linkage; X$^1$ and X$^2$ are each independently an oxygen-linked saccharide; Z is hydrogen (H) or —CH$_2$—X$^3$, and X$^3$ is an oxygen-linked saccharide,

[Formula 2]

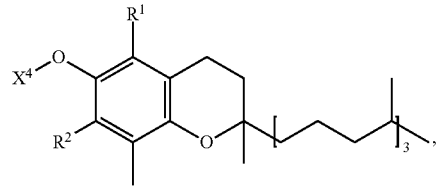

where R$^1$ and R$^2$ are each independently hydrogen (H) or CH$_3$; and X$^4$ is a glucose-centered, branched pentasaccharide.

2. The compound of claim 1, wherein each saccharide of Formula 1 is glucose or maltose.

3. The compound of claim 1, wherein R$^1$ and R$^2$ are CH$_3$.

4. The compound of claim 1, wherein R$^1$ and R$^2$ are CH$_3$; L is —CH$_2$CH$_2$— or —NHCOCH$_2$—; and Z is hydrogen.

5. The compound of claim 1, wherein R$^1$ and R$^2$ are CH$_3$; L is —CH$_2$— or —CH$_2$OCH$_2$CH$_2$—; and Z is —CH$_2$—X$^3$.

6. The compound of claim 1, wherein the compound is one of Formulas 3 to 7 below:

[Formula 3]

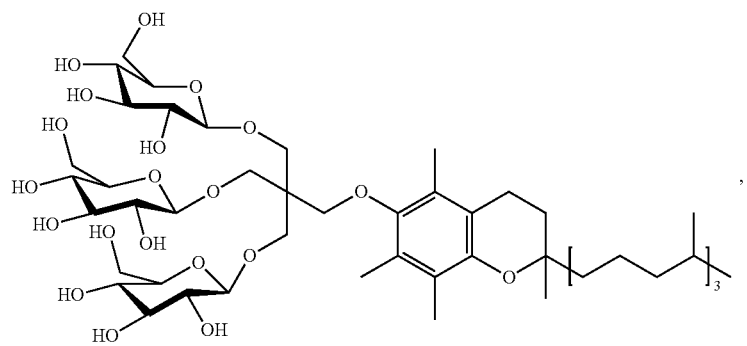

-continued

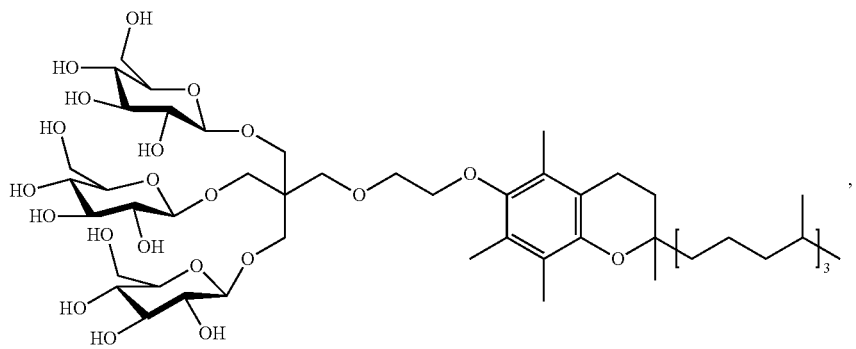
[Formula 4]

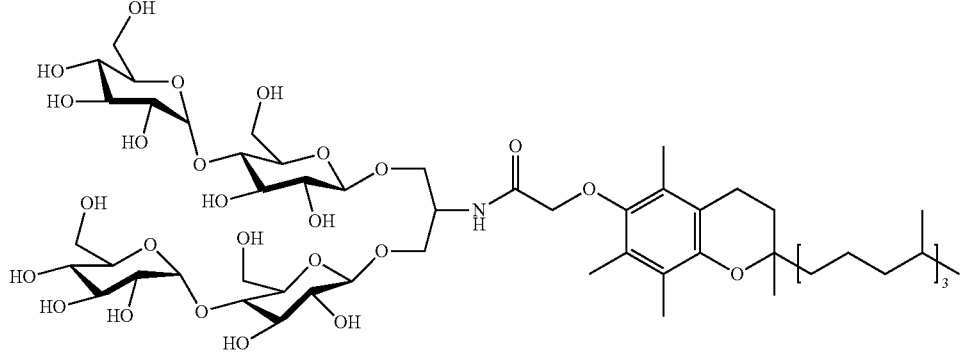
[Formula 5]

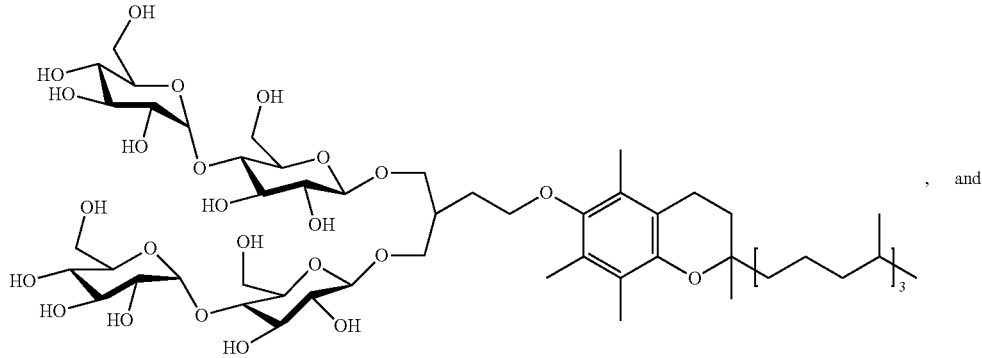
[Formula 6]
, and

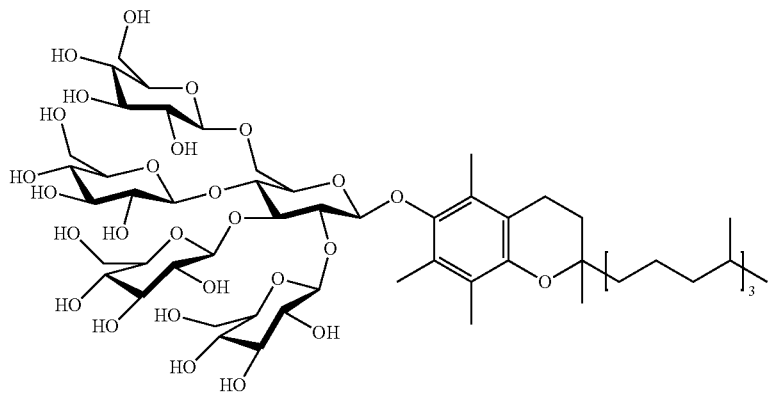
[Formula 7]

7. The compound of claim 1, wherein the compound is an amphipathic molecule for extracting, solubilizing, stabilizing or analyzing a membrane protein.

8. The compound of claim 1, wherein the compound has a critical micelle concentration (CMC) in an aqueous solution of 0.1 to 10 μM.

9. A composition for extracting, solubilizing, stabilizing or analyzing a membrane protein, comprising the compound of claim 1.

10. The composition of claim 9, wherein the composition is a formulation in the form of a micelle, liposome, emulsion or nanoparticle.

11. A method of preparing a compound represented by Formula 1 below, comprising:
1) introducing a linker having a —CH₂—, —CH₂CH₂—, —NHCOCH₂— or —CH₂OCH₂CH₂— structure to a vitamin E tocopherol;
2) producing an alcohol group by reacting the product of Step 1) with 4-(bromomethyl)-methyl-2,6,7-trioxabicyclo[2,2,2]-octane or diethyl malonate and performing reduction;
3) introducing a protecting group-attached saccharide by performing glycosylation on the product of Step 2); and
4) performing deprotection on the product of Step 3):

[Formula 1]

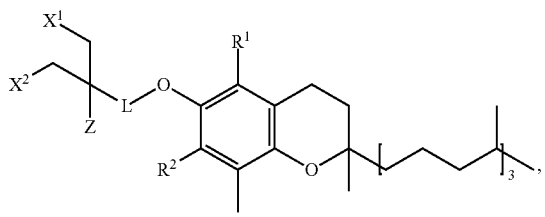

where R¹ and R² are each independently hydrogen (H) or CH₃; L is —CH₂—, —CH₂CH₂—, —NHCOCH₂—, —CH₂OCH₂CH₂— or a direct linkage; X¹ and X² are each independently an oxygen-linked saccharide; Z is hydrogen (H) or —CH₂—X³, and X³ is an oxygen-linked saccharide.

12. A method of preparing a compound represented by Formula 2 below, comprising repeatedly performing the steps including 1) introducing a protecting group-attached saccharide by performing glycosylation on a vitamin E tocopherol; and 2) performing deprotection on the product of Step 1):

[Formula 2]

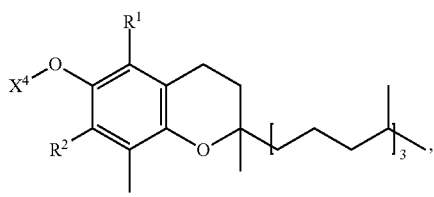

where R¹ and R² are each independently hydrogen (H) or CH₃; and X⁴ is a glucose-centered, branched pentasaccharide.

13. The method of claim 11, wherein R¹ and R² are CH₃; and each saccharide is glucose or maltose.

14. A method of extracting, solubilizing, stabilizing, crystallizing or analyzing a membrane protein, comprising treating a membrane protein with the compound represented by Formula 1 or 2 below in an aqueous solution:

[Formula 1]

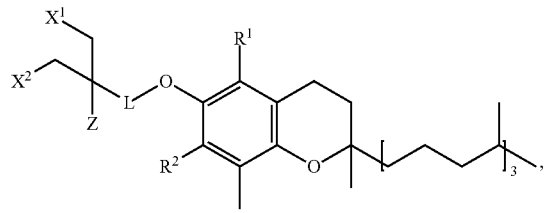

where R¹ and R² are each independently hydrogen (H) or CH₃; L is —CH₂—, —CH₂CH₂—, —NHCOCH₂—, —CH₂OCH₂CH₂— or a direct linkage; X¹ and X² are each independently an oxygen-linked saccharide; Z is hydrogen (H) or —CH₂—X³, and X³ is an oxygen-linked saccharide,

[Formula 2]

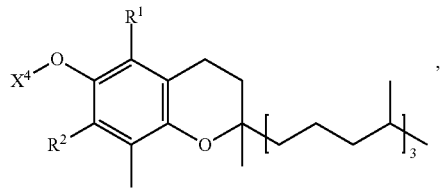

where R¹ and R² are each independently hydrogen (H) or CH₃; and X⁴ is a glucose-centered, branched pentasaccharide.

15. The method of claim 14, wherein R¹ and R² are each independently hydrogen (H) or CH₃; L is —CH₂CH₂— or —NHCOCH₂—; and Z is hydrogen.

16. The method of claim 14, wherein R¹ and R² are CH₃; L is —CH₂— or —CH₂OCH₂CH₂—; and Z is —CH₂—X³.

17. The method of claim 14, wherein the membrane protein is a complex of light harvesting-I and a reaction center (LHI-RC complex), a uric acid-xanthine/H⁺symporter (UapA), melibiose permease (MelB), a leucine transporter (LeuT), a G-protein coupled receptor (GPCR) or a combination of two or more thereof.

* * * * *